United States Patent [19]

Powers et al.

[11] Patent Number: 5,543,396
[45] Date of Patent: Aug. 6, 1996

[54] PROLINE PHOSPHONATE DERIVATIVES

[75] Inventors: James C. Powers, Atlanta, Ga.; Bogdan Boduszek, Wroclaw, Poland; Jozef Oleksyszyn, Arlington, Mass.

[73] Assignee: Georgia Tech Research Corp., Atlanta, Ga.

[21] Appl. No.: 234,181

[22] Filed: Apr. 28, 1994

[51] Int. Cl.⁶ ............ A61K 38/00; A61K 31/67; A01N 57/00; C07F 5/02
[52] U.S. Cl. ............ 514/19; 514/87; 514/89; 514/94; 548/412; 548/111; 546/21; 540/542; 540/450; 544/53; 544/57; 544/88; 544/106; 558/170
[58] Field of Search ............ 514/87, 89, 94, 514/101; 548/412, 111; 546/21, 450; 540/542; 544/53, 57, 88, 106; 558/170

[56] References Cited

U.S. PATENT DOCUMENTS 4,443,609  4/1984  Alink et al. ............ 548/111

OTHER PUBLICATIONS

Callebaut, C. et al., T Cell Activation Antigen, CD26, as a Cofactor for Entry of HIV in CD4+Cells, Science 1993, 262, pp. 2045–2050.
Oleksyszyn et al., Synthesis, 1979, 985–986.
Szewczyk et al., Synthesis, 1982, 409–414.
Bartlett et al., Bioorg. Chem., 1986, 14, 356–377.
Petrillo, E. W. et al., Synthesis of 2–Phosphopyrrolidine and Its Substitution for Proline, Tet. Lett. 1979, 51, 4929.
Vo–Quang, Y. et al., J. Med. Chem. 1986, 43, 579–581.
Kafarski, P. et al., Tetrahedron, 1987, 43, 799–803.
Lamden et al., Biochem. Biophys. Res. Commun., 1983, 112, 1085–1090.
Oleksyszyn et al., Irreversible Inhibition of Serine Proteases by Peptidyl Derivatives of α–Aminoalkylphosphonate Diphenyl Esters, Biochem. Biophys. Res. Commun. 1989, 161, 143–149.
Fastrez et al., Tet. Lett. 1989, 30, 6861–6864.
Oleksyszyn et al., Irreversible Inhibition of Serine Proteases by Peptide Derivatives of (α–Aminoalkyl) phosphonate Diphenyl Esters, Biochem. 1991, 30, 485–493.
Walsh, E.N., Conversion o fTertiary Phoshoites to Secondary Phosphonates, J. Am. Chem. Soc. 1959, 81, 3023–3026.
McCombi, H. et al., Esters Containing Phosphorous, Part I, J. Chem. Soc. 1945, 381.
Nomura, Y. et al., One Step Synthesis and Structural Confirmation with 1–Pyrroline Trimer, Chem. Lett. 1977, 696–696.
ASM News vol. 56 p. 368 (1990).
Jaroff, Time May 23, 1988 p. 56.
Sandstrom et al., Drugs vol. 34 p. 372 (1987).
Blumenstein et al., Biochem. Biophys. Res. Comm. vol. 163 p. 980 (1989).
Renaud et al. Angewandte Chemie vol. 98 p. 836 (1986).
Seebach et al., Helvetica Chimica Acta vol. 72 p. 401 (1989).
Powers et al., Proteases, Protease Inhibitors and Protease–Derived Peptides vol. 42 pp. 3–18 (1993).
Nagatsu et al. Anal. Biochem. vol. 74 pp. 466–476 (1976).
Kabota et al., Clin. Exp. Immunol. vol. 96 p. 292 (1994).

*Primary Examiner*—Toni R. Scheiner
*Assistant Examiner*—Sheela J. Huff
*Attorney, Agent, or Firm*—DeVeau, Colton & Marquis

[57] ABSTRACT

Peptidyl derivatives of diesters of α-aminoalkylphosphonic acids, particularly those with proline or related structures, their use in inhibiting serine proteases with chymotrypsin-like, trypsin-like, elastase-like, and dipeptidyl peptidase IV specificity and their roles as anti-inflammatory agents, anti-coagulants, and anti-tumor agents.

13 Claims, No Drawings

PROLINE PHOSPHONATE DERIVATIVES

STATEMENT OF GOVERNMENT INTEREST

This invention was made with government support under Grants No. HL34035 and HL29307 awarded by the National Heart, Lung and Blood Institute of the National Institutes of Health. The United States government may have certain rights in this invention.

BACKGROUND OF THE INVENTION

1. Field of the Invention

This invention relates to a novel class of peptidyl derivatives of aromatic diesters of α-aminoalkylphosphonic acids useful for selectively inhibiting elastase, selectively inhibiting chymotrypsin-like enzymes, selectively inhibiting trypsin-like enzymes and selectively inhibiting dipeptidyl peptidase IV (DPP-IV). The diesters of α-aminoalkylphosphonic acids are analogues of natural α-amino acids. This invention also relates to a method for controlling tumor invasion, treating inflammation and controlling blood coagulation in patients using the novel compounds of the present invention. We have found that peptidyl derivatives of aromatic diesters of α-aminoalkylphosphonic acids are potent inhibitors of chymotrypsin-like enzymes, elastases, blood coagulation enzymes, tryptases, kallikreins, and therefore they are useful as anti-tumor, anti-inflammatory and anticoagulant agents. We have also found that dipeptide proline phosphonates are inhibitors of dipeptidyl peptidase IV (DPP-IV, enzyme number EC 3.4.14.5, also known as CD26) and are thus useful in treatment of immune system disorders and acute respiratory distress syndrome (AIDS).

2. Description of the Related Art

Serine proteases play critical roles in several physiological processes such as digestion, blood coagulation, complement activation, fibrinolysis, and reproduction. Serine proteases are not only a physiological necessity, but also a potential hazard if they are not controlled. Blood coagulation serine proteases are responsible for vascular clotting, cerebral infarction and coronary infarction. Chymotrypsin-like enzymes and plasmin are involved in tumor invasion, tissue remodeling, and clot dissociation. Uncontrolled proteolysis by other serine proteases such as elastase may cause pancreatitis, emphysema, rheumatoid arthritis, inflammation and adult respiratory distress syndrome. Accordingly, specific and selective inhibitors of these proteases should be potent anticoagulants, anti-inflammatory agents and anti-tumor agents useful in the treatment of protease-related diseases. In vitro proteolysis by trypsin, chymotrypsin or the elastase family is a serious problem in the production, purification, isolation, transport or storage of peptides and proteins.

Dipeptidyl peptidase IV (DPP-IV, EC 3.4.14.5, CD26) is a post-proline cleaving enzyme which will remove the dipeptides AA-Pro (AA=amino acid residue) from the N-terminus of proteins or polypeptides. DPP-IV has been found in a variety of mammalian cells and tissues including kidney, placenta, blood plasma and on the surface of certain T-lymphocyte subsets. Despite extensive studies, the biological role of DPP-IV in mammalian systems has not been completely established, although a number of functions have been postulated. DPP-IV may participate in the metabolism and uptake of proline-containing peptides in the intestine and kidney and may be involved in fibronectin-mediated cell movement and adhesion. DPP-IV may also play a role in the metabolism or catabolism of collagen which has a high frequency of Gly-Pro sequences. DPP-IV in human plasma has been shown to cleave N-terminal Tyr-Ala from growth hormone-releasing factor and cause inactivation of this hormone. DPP-IV is also involved in T-cell activation and regulation of T-cell proliferation. Thus, inhibitors of DPP-IV may have therapeutic utility in the modulation of the rejection of transplanted tissue by the host organism. Recently DPP-IV or CD26 has been postulated to act as a cofactor for entry into HIV in CD4$^+$ cells (Callebaut, C., Krust, B., Jacotot, E., Hovanessian, A. G. T cell activation antigen, CD26, as a cofactor for entry of HIV in CD4$^+$ cells. *Science.* 1993, 262, 2045–2050). Thus inhibitors of DPP-IV should have therapeutic utility in the treatment of AIDS.

BRIEF SUMMARY OF THE INVENTION

The proline phosphonates derivatives of this invention have the following general structure:

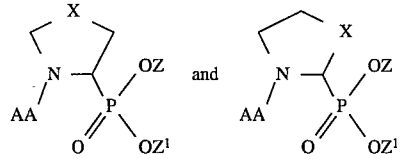

or a pharmaceutically acceptable salt thereof, wherein Z and $Z^1$ are the same or different and are selected from the group consisting of $C_{1-6}$ perfluoroalkyl, phenyl, phenyl substituted with J, phenyl disubstituted with J, phenyl trisubstituted with J, and pentafluorophenyl; J is selected from the group consisting of halogen, $C_{1-6}$ alkyl, $C_{1-6}$ perfluoroalkyl, $C_{1-6}$ alkoxy, $NO_2$, CN, OH, $CO_2H$, amino, $C_{1-6}$ alkylamino, $C_{2-12}$ dialkylamino, $C_{1-6}$ acyl, and $C_{1-6}$ alkoxy—CO—, and $C_{1-6}$ alkyl—S—; X is selected from the group consisting of (a) a single bond, (b) —$CH_2$—, (c) —$CH_2CH_2$—, (d) —$CH_2CH_2CH_2$—, (e) —$CH_2CH_2CH_2CH_2$—, (f) —Y—, (g) —$CH_2$—Y—, (h) —Y—$CH_2$—, and (i) —H, H—, wherein Y is O or S; and AA is selected from the group consisting of (a) the structure $NH_2$—CHR—CO— where R is selected from the group consisting of $C_{1-6}$ alkyl and $C_{1-6}$ fluorinated alkyl, (b) a side chain blocked or unblocked alpha amino acid residue with the L, D or DL configuration at the α-carbon atom selected from the group consisting of alanine, valine, leucine, isoleucine, proline, methionine, methionine sulfoxide, phenylalanine, tryptophan, serine, threonine, cysteine, tyrosine, asparagine, glutamine, aspartic acid, glutamic acid, lysine, arginine, histidine, phenylglycine, norleucine, norvaline, alpha-aminobutyric acid, citrulline, hydroxyproline, ornithine, homoarginine, O-methylserine, O-ethylserine, S-methylcysteine, S-ethylcysteine, S-benzylcysteine, $NH_2$—$CH(CH_2CHEt_2)$—COOH, alphaaminoheptanoic acid, $NH_2$—$CH(CH_2$-1-napthyl)—COOH, $NH_2$—$CH(CH_2$-2-napthyl)—COOH, $NH_2$—$CH(CH_2$-cyclohexyl)—COOH, $NH_2$—$CH(CH_2$-cyclopentyl)—COOH, $NH_2$—$CH(CH_2$-cyclobutyl)—COOH, $NH_2$—$CH(CH_2$-cyclopropyl)—COOH, 5,5,5-trifluoroleucine, and hexafluoroleucine, (c) an amino acid residue selected from the group consisting of beta-alanine, glycine, epsilon-aminocaproic acid, and sarcosine, (d) H, and (e) $C_6H_5CH_2OCO$—.

A therapeutically effective amount of these compounds can be used to inhibit dipeptidyl peptidase IV in mammals.

A therapeutically effective amount of these compounds can be used to treati AIDS in mammals.

A therapeutically effective amount of these compounds can be used to prevent tissue transplant rejection in mammals.

It is an object of this invention to define a novel group of specific inhibitors for trypsin, elastase, chymotrypsin and other serine proteases. Inhibitors are compounds that can reduce or eliminate the catalytic activity of the enzyme. Trypsin and trypsin-like enzymes normally cleave peptide bonds in proteins and peptides where the amino acid residue on the carbonyl side of the split bond ($P_1$ residue) is Lys or Arg. Elastase and elastase-like enzymes cleave peptide bonds where the $P_1$ amino acid is Ala, Val, Ser, Leu and other similar amino acids. Chymotrypsin and chymotrypsin-like enzymes hydrolyze peptide bonds where the $P_1$ amino acid is Trp, Tyr, Phe, Met, Leu or other amino acid residue which contain an aromatic or large alkyl side chain. All of the above enzymes have extensive secondary specificity and recognize amino acid residues removed from the $P_1$ residue.

It is a further object of this invention to define new protease inhibitors, especially inhibitors for chymotrypsin and chymotrypsin-like enzymes, elastase inhibitors, blood coagulation enzyme inhibitors and tryptase inhibitors. These inhibitors are useful for controlling tumor invasion, blood coagulation and various inflammatory conditions mediated by serine proteases. The inhibitors of this invention are useful for treating diseases such as vascular clotting, inflammations, tumor invasion, pancreatitis, emphysema or infantile and adult respiratory distress syndrome. The inhibitors of this invention are also useful for controlling hormone processing by serine proteases and for treating diseases related to tryptases such as inflammation and skin blistering.

It is yet another object of this invention to define a novel group of specific inhibitors useful in vitro for inhibiting trypsin, elastase, chymotrypsin and other serine proteases of similar specificity. Such inhibitors could be used to identify new proteolytic enzymes encountered in research. They can be used in research and industrially to prevent undesired proteolysis that occurs during the production, isolation, purification, transport and storage of valuable peptides and proteins. Such proteolysis often destroys or alters the activity and/or function of the peptides and proteins. Uses can include the addition of the inhibitors to antibodies, enzymes, plasma proteins, tissue extracts or other proteins and peptides which are widely sold for use in clinical analyses, biomedical research, and for many other reasons.

It is yet another objective of this invention to define a novel group of specific inhibitors for DPP-IV. The inhibitors are useful for controlling the immune system, inhibiting the process of organ transplant rejection, for treatment of AIDS, and related disorders.

These and other objects are accomplished by the present invention which defines novel peptidyl derivative of aryl diesters of α-aminoalkylphosphonic acids. These phosphonate derivatives are potent inhibitors of serine proteases including chymotrypsin-like enzymes, trypsin-like enzymes, elastase-like enzymes, DPP-IV and other enzymes with other substrate specificities. The phosophonates are stable in buffer or plamsa, and inhibit the serine proteases to give stable inhibited enzyme derivatives. The phosphonates can be used both in vitro and in vivo.

DETAILED DESCRIPTION OF THE INVENTION

Peptidyl derivatives of aryl diesters of α-aminoalkylphosphonic acids have be found to be excellent inhibitors of several serine proteases including bovine thrombin, human factor XIIa, human plasma kallikrein, bovine trypsin, rat skin tryptase, human leukocyte elastase, porcine pancreatic elastase, bovine chymotrypsin, human leukocyte cathepsin G, DPP-IV, and rat mast cell protease II. The diesters of α-aminoalkylphosphonic acids are analogues of natural α-amino acids and are designated by the generally accepted three letter abbreviations for the amino acid followed by the superscript P. For example diphenyl α-(N-benzyloxycarbonylamino)ethylphosphonate which is related to alanine is abbreviated as $Cbz\text{-}Ala^P(OPh)_2$.

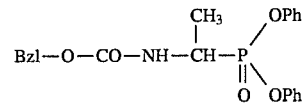

Complete Structure of $Cbz-Ala^P(OPh)_2$

Peptidyl derivatives of aryl diesters of α-aminoalkylphosphonic acids inhibit serine proteases by reaction with the active site serine to form "phosphonylated" enzymes, which due to the similarity of phosphorus atom to the tetrahedral intermediate formed during peptide hydrolysis, show remarkable stability. The enzyme catalytic apparatus is required to activate the phosphorus atom for nucleophilic substitution and reaction with enzyme. The activation is mainly due to precise interaction with the $S_1$ pocket of various serine proteases. The following figure shows the reaction course of a phosphonate with a serine protease. The phosphonate first binds to the enzyme (below left) and then reacts to form a covalent bond with the active site serine residue (below right). Slow aging can take place with loss of the phenoxy group (below center).

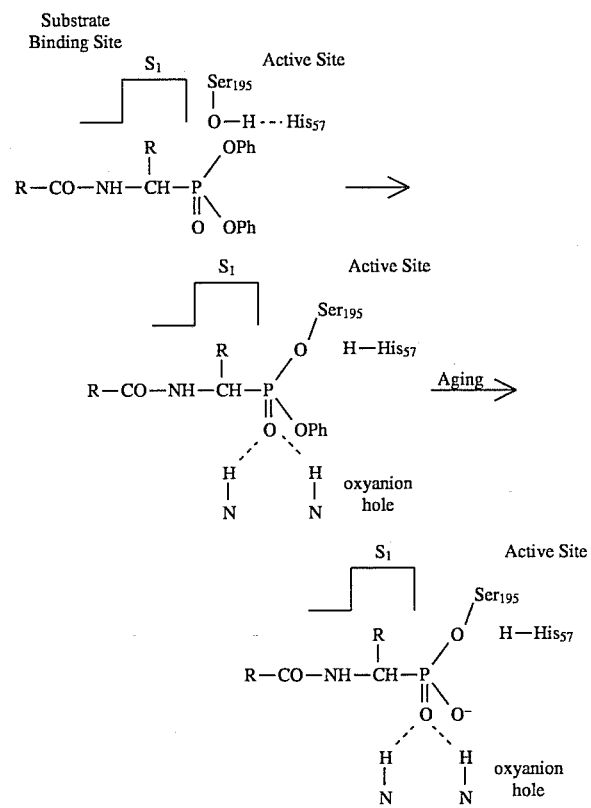

Peptides with a C-terminal phosphonate residue which is an analog of valine (e.g. $Val^P(OPh)_2$) are potent and specific irreversible inhibitors of elastase and elastase-like enzymes. The peptides with C-terminal phosphonate residues related to phenylalanine, other aromatic amino acids or amino acids with long aliphatic side chains are potent and specific inhibitors of chymotrypsin and chymotrypsin-like enzymes. The peptides with C-terminal phosphonate residues related to ornithine, arginine or containing a C-terminal diphenyl ester of α-amino-α-(4-amidinophenyl)methanephosphonate are specific and potent inhibitors of trypsin and trypsin-like enzymes. Dipeptides with the C-terminal phosphonate residues related to proline or homoproline are specific and potent inhibitors of DPP-IV. The structures of two inhibitors are shown below. The dipeptide phosphonate on the left has a proline phosphonate derivative (abbreviated -Pro$^P$-) at the C-terminal end of the dipeptide, while the derivative on the right has a homoproline phosphonate (or piperidyl phosphonate, abbreviated -Pip$^P$-) as the C-terminal residue.

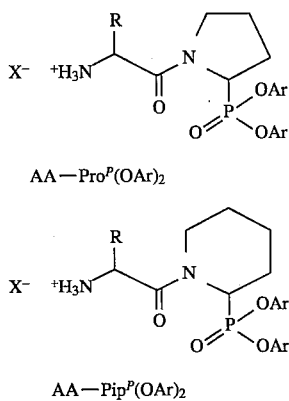

AA—Pro$^P$(OAr)$_2$

AA—Pip$^P$(OAr)$_2$

Additional specificity as well as increased activation toward reaction with the enzyme can be introduced into the inhibitor molecule by variation of the amino acid sequence in the peptide portion of the structure. In fact there is a good agreement between the sequence of enzyme substrates such as a peptidyl p-nitroanilides and the sequence of an effective peptidyl phosphonate inhibitor. The best inhibitors have the sequence of the best peptidyl p-nitroanilide substrate for a particular enzyme. For example, the best inhibitor for chymotrypsin and chymotrypsin-like enzymes is Suc-Val-Pro-Phe$^P$(OPh)$_2$ which has an amino acid sequence that is analogous to Suc-Val-Pro-Phe-NA, an excellent substrate for these enzymes. With human leukocyte elastase, the two best inhibitors (MeO-Suc-Ala-Ala-Pro-Val$^P$(OPh)$_2$ and Boc-Val-Pro-Val$^P$(OPh)$_2$) have an amino acid sequence similar to MeO-Suc-Ala-Ala-Pro-Val-NA and Boc-Val-Pro-Val-NA, two excellent substrates for this enzyme. For bovine thrombin, the best phosphonate inhibitor is diphenyl Boc-D-Phe-Pro-amino(4-amidinophenyl) methanephosphonate hydrochloride, which corresponds to Boc-D-Phe-Pro-Arg-NA, which is excellent substrate for thrombin, and D-Phe-Pro-Arg-H which is an excellent peptide aldehyde inhibitor of thrombin and an anticoagulant. Since good substrate sequences are known in the literature for other serine proteases, it is possible to predict the structure of additional excellent phosphonate inhibitors for these enzymes. It is also possible to design good phosophonate inhibitors for serine proteases based on on the peptide sequences found in other potent reversible and irreversible inhibitors for those same serine proteases reported in the literature Examples of phosphonate inhibitors for various enzymes are given below:

| | |
|---|---|
| Cbz—Gly—Leu—Phe$^P$(OZ)$_2$ | for cathepsin G and RMCP II |
| MeO—Suc—Ala—Ala—Pro—Met$^P$(OZ)$_2$ | for Cathepsin G |
| Suc—Pro—Leu—Phe$^P$(OZ)$_2$ and Boc—Ala—Ala—Phe$^P$(OZ)$^2$ | for RMCP I |
| Boc—Gly—Leu—Phe$^P$(OZ)$_2$, Suc—Phe—Leu—Phe$^P$(OZ)$_2$ | for human and dog skin chymase |
| Boc—Ala—Ala—Glu$^P$(OZ)$_2$ | for S. aureus V-8 protease |
| Cbz—Gly—Gly—Pro$^P$(OZ)$_2$ | for human prolyl endopeptidase |
| Ala—Pro$^P$(OZ)$_2$ | for DPP IV |
| Suc—Ala—Ala—Pro—Val$^P$(OZ)$_2$ | for PPE |
| Suc—Lys(Cbz)—Val—Pro—Val$^P$(OZ)$_2$, adamantyl-SO$_2$— Lys(COCH$_2$CH$_2$CO$_2$H)—Ala— Val$^P$(OZ)$_2$,adamantyl-CH$_2$CH$_2$OCO— Glu(O-t-Bu)—Pro—Val$^P$(OZ)$_2$, adamantyl-SO$_2$—Lys(CO—C$_6$H$_4$CO$_2$H)— Ala—Val$^P$(OZ)$_2$ | for human leukocyte (neutrophil) elastase |
| Suc—Ala—Ala—Pro—Leu$^P$(OZ)$_2$ | for elastolytic proteinase from "Schistosoma mansoni" |
| Glu—Phe—X and Dns—Ala—Phe—X | for plasmin |
| D—Val—Gly—X and Dns—Glu—Gly—X | for factor Xa |
| Cbz—Phe—X and Cbz—Trp—X | for porcine pancreatic and human plasma kallikreins |
| Cbz—Lys—X | for human skin tryptase |
| Cbz—Gly—X | for human lung tryptase |
| Cbz—Ile—Ala—Gly—X | for factors IXa, Xa, XIa, XIIa and bovine plasma kallikrein |
| Glu—Gly—X | for urokinase |
| Dns—Phe—Pro—X | for plasminogen activator |
| Dns—Ile—Pro—X | for activated protein C |
| Cbz—Trp—X | for bovine factor IXa |
| Cbz—Gly—X | for bovine factor Xa and XIa |
| Cbz—Phe—X | for bovine factor XIIa |
| Cbz—Phe—Gly—X | for trypsin | where Z represents an aryl group, a substituted aryl group or a highly fluorinated alkyl group and X represents Arg$^P$(OZ)$_2$ or an aryl diester of α-amino-α-(4-amidinophenyl)methanephosphonate [NH$_2$—CH(AmPh)PO(OZ)$_2$].

The inhibitory potency of peptidyl derivatives of aryl diesters of α-aminoalkylphosphonic acids is also determined by the electronic property of the Z group. More electron withdrawing groups such as nitro, cyano, halogen, etc. on the aryl ring can make the phosphorus atom in the inhibitor more electrophilic and accelerate reaction with the active site serine of the serine protease. Reactivity toward serine proteases can also be obtained by using derivatives where the Z groups are highly fluorinated alkyl groups. However increased reactivity can also result in low chemical stability and in extreme cases, compounds may be too hydrolyrically unstable for practical purposes if the Z group is too electronegative. Phosphonates where the Z group is not sufficiently electron withdrawing will be chemically very stable and will react very slowly with serine proteases or not at all. Such non-reactive inhibitors would include derivatives where Z is simple alkyl groups (e.g. peptidyl derivatives of alkyl diesters of α-aminoalkylphosphonic acids). Thus the phosphonate ester groups (Z) should represent a balance between these two competing factors and we find that diphenyl esters (Z=Ph) are one way to obtain a balance between increased reactivity and stability in solution.

Diphenyl esters of α-aminoalkylphosphonate can be synthesized by a previously described method (Oleksyszyn et al., 1979, Synthesis, 985, incorporated by reference). Di(substituted phenyl)esters of α-aminoalkylphosphonate can also be prepared by the same procedure using iris(substituted phenyl) phosphite instead of triphenyl phosphite. Perfluoroalkyl diesters can be synthesized by a method involving transesterification (Szewczyk et al., Synthesis, 1982, 409–414, incorporated by reference). Alternatively, the synthesis of diesters of α-aminoalkylphosphonic acids and their peptides can be performed by esterification of the phosphonic acid moiety as described previously (Bartlett et al., 5 HCl.Pip$^P$(OPh-4-F)$_2$ 6 HCl.Ala-Pro$^P$(OPh)$_2$ 7 AcOH.Ala-Pip$^P$(OPh)$_2$ 8 AcOH.Ala-Pip$^P$(OH)(OPh)

9 HBr.Phe-Pro$^P$(OPh)$_2$ 10 2HBr.Lys-Pro$^P$(OPh)$_2$ 11 2HCl.Lys-Pip$^P$(OPh)$_2$

12 HCl.Ala-Pro$^P$(OPh-4Cl)$_2$

13 HCl.Ala-Pip$^P$(OPh-4Cl)$_2$

14 HCl.Ala-Pip$^P$(OPh-4-F)$_2$

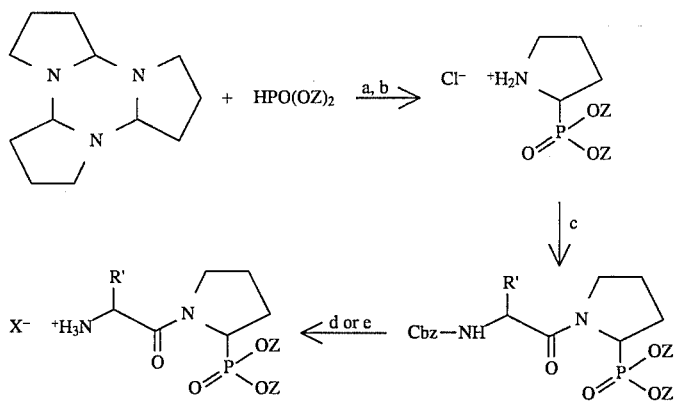

$^a$Reagents: (a) heat under argon; (b) HCl gas in ether; (c) Cbz—NHCHR'COOH, DCC; (d) Pd/C, H$_2$, H$^+$ (e) 30% HBr/AcOH Bioorg. Chem., 1986, 14, 356–377, incorporated by reference).

The dipeptides which contain 2-pyrrolidylphosphonate (proline phosphonate) or 2-piperidylphosphonate (homoproline phosphonate) were synthesized using the reactions outlined in the following scheme. The proline phosphonate HCl.Pro$^P$(OR)$_2$ was synthesized by reaction of diphenyl phosphite or di-(4-chlorophenyl) phosphite with 1-pyrroline trimer (Petrillo, E. W., Spitzmiller, E. R. Synthesis of 2-Phosphopyrrolidine and Its Substitution for Proline in an Inhibitor of Angiotensin-Converting Enzyme, Tet. Lett. 1979, 51, 4929). Subsequent coupling of HCl.Pro$^P$(OR)$_2$ (HCl.Pro$^P$(OPh)$_2$, 1 or HCl.Pro$^P$(OPh-4-Cl)$_2$,3) with the N-blocked amino acid Cbz-AA-OH using the DCC method gave the dipeptide phosphonate Cbz-AA-Pro$^P$(OR)$_2$. Deblocking of the dipeptides was accomplished by hydrogenolysis in the presence of acid or by the use of 30% HBr in AcOH to give compounds 6, 9, 10, and 12. Similarly, the homoproline derivative Pip$^P$(OR)$_2$.HCl(2, 4, or 5) was synthesized by reaction of diphenyl phosphite or di-(4-halophenyl) phosphite with 2,3,4,5-tetrahydropyridine trimer (Solodenko, V. A., Kukhar, V. P. Synthesis of DL-(2-Piperidyl) Phosphonic Acid, Zh. Obsh. Khim. 1987, 57, 2392). The intermediate Pip$^P$(OR)$_2$.HCl was then coupled with Cbz-AA-OH using the DCC method to give the dipeptides Cbz-AA-Pip$^P$(OR)$_2$. Subsequent deblocking of Cbz-AA-Pip$^P$(OR)$_2$ with hydrogenolysis in the presence of acid or HBr in AcOH gave compounds 7, 12, 13, and 14.

1 HCl.Pro$^P$(OPh)$_2$ 2 (HCl.Pip$^P$(OPh)$_2$

3 HCl.Pro$^P$(OPh-4-Cl)$_2$

4 HCl.Pip$^P$(OPh-4-Cl)$_2$,

The diphenyl phosphonate moiety is very resistent to chemical hydrolysis and at pH 7.5 we did not observe any hydrolysis after several days (monitored by $^{31}$P NMR). Furthermore, they show excellent stability in human plasma. For example Suc-Val-Pro-Phe$^P$(OPh)$_2$ has a hydrolysis half-time in human plasma of about 20 hrs. These experiments demonstrate that the phosphonate inhibitors are remarkably stable in buffer and plasma. Thus they can be used under a variety of conditions. Phosphonates have the additional advantage of being very stable in plasma and will have a high effectiveness in 10 vivo due to their long lifetimes. Additionally, the inhibitor-enzyme complex is very stable and the enzyme did not regain any activity after several hours in the case of chymotrypsin and after several days no recovery of activity was observed in the the cases of elastases and trypsin. These experiments show that it is possible to decrease or eliminate the enzyme activity and biological function of serine proteases for extended time periods.

Either racemic mixtures of the diphenyl α-aminoalkylphosphonate residue or pure diastereomers can be used in the inhibitor structures. The racemic compounds are more easily synthesized and are obtained from less expensive starting materials. The pure optically active α-aminoalkylphosphonate derivatives required in the synthesis are more difficult to synthesize and require more expensive starting materials. In the case of the peptidyl phosphonate inhibitors which are mixtures of two diastereomers, only one will usually react with the enzymes. The pure diastereomers will possess higher inhibition rates and could be used at lower concentrations.

Peptidyl derivatives of aryl diesters of α-aminoalkylphosphonates may be used in vivo to treat diseases resulting from abnormal or uncontrolled blood coagulation or diseases caused by uncontrolled proteolysis by elastase, chymotrypsin, trypsin and related serine proteases. These inhibitors may be used in vitro to prevent proteolysis which occurs in the process of the production, isolation, purification, storage or transport of peptides and proteins.

The novel peptidyl derivatives of aryl diesters α-aminoalkylphosphonates of the present invention have the following structural formula:

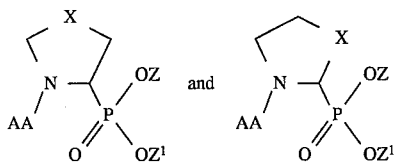

or a pharmaceutically acceptable salt, wherein

Z and $Z^1$ are the same or different and are selected from the group consisting of $C_{1-6}$perfluoroalkyl, phenyl, phenyl substituted with J, phenyl disubstituted with J, phenyl trisubstituted with J, and pentafluorophenyl;

J is selected from the group consisting of halogen, $C_{1-6}$ alkyl, $C_{1-6}$ perfluoroalkyl, $C_{1-6}$ alkoxy, $NO_2$, CN, OH, $CO_2H$, amino, $C_{1-6}$ alkylamino, $C_{2-12}$ dialkylamino, $C_{1-6}$ acyl, and $C_{1-6}$ alkoxy—CO—, and $C_{1-6}$ alkyl—S—;

X is selected from the group consisting of
(a) a single bond,
(b) —$CH_2$—,
(c) —$CH_2CH_2$—,
(d) —$CH_2CH_2CH_2$—,
(e) —$CH_2CH_2CH_2CH_2$—,
(f) —Y—,
(g) —$CH_2$—Y—,
(h) —Y—$CH_2$—, and
(i) —H, H—,
wherein Y is O or S; and AA is selected from the group consisting of
(a) the structure $NH_2$—CHR—CO— where R is selected from the group consisting of $C_{1-6}$ alkyl and $C_{1-6}$ fluorinated alkyl,
(b) a side chain blocked or unblocked alpha amino acid residue with the L, D or DL configuration at the α-carbon atom selected from the group consisting of alanine, valine, leucine, isoleucine, proline, methionine, methionine sulfoxide, phenylalanine, tryptophan, serine, threonine, cysteine, tyrosine, asparagine, glutamine, aspartic acid, glutamic acid, lysine, arginine, histidine, phenylglycine, norleucine, norvaline, alpha-aminobutyric acid, citrulline, hydroxyproline, ornithine, homoarginine, O-methylserine, O-ethylserine, S-methylcysteine, S-ethylcysteine, S-benzylcysteine, $NH_2$—CH($CH_2CHEt_2$)—COOH, alpha-aminoheptanoic acid, $NH_2$—CH($CH_2$-1-napthyl)—COOH, $NH_2$—CH($CH_2$-2-napthyl)—COOH, $NH_2$—CH($CH_2$-cyclohexyl)—COOH, $NH_2$—CH($CH_2$-cyclopentyl)—COOH, $NH_2$-CH($CH_2$-cyclobutyl)—COOH, $NH_2$—CH($CH_2$-cyclopropyl)—COOH, 5,5,5-trifluoroleucine, and hexafluoroleucine,
(c) an amino acid residue selected from the group consisting of beta-alanine, glycine, epsilon-aminocaproic acid, and sarcosine,
(d) H, and
(e) $C_6H_5CH_2OCO$—.

This invention also includes the use of the novel phosphonate compounds described above for inhibiting dipeptidyl peptidase IV in mammals by treatment of a mammal with a therapeutically effective amount of the novel phosphonate compound.

The blocking groups which may be present on —HN—CH(R)—P(O)— or on the amino acid AA are those well known in the art of peptide synthesis. The particular choice of the blocking group used in the compounds of the invention depends on several factors, including the blocking group's affect on enzyme specificity, its affect on phosphonate solubility, and its utility during synthesis. Suitable blocking groups include but are not limited to carbobenzyloxy (Cbz), benzoyl, t-butyloxycarbonyl (Boc), glutaryl, p-tolylsulfonyl (Tos), methoxysuccinyl (MeO-Suc), and succinyl.

The —HN—CH(R)—P(O)— residue is derived from a blocked or unblocked alpha amino acid residue —HN—CH(R)—CO— whose alpha carbonyl group has been replaced by a P(O) group. The R group is the side chain of the alpha amino acid. The alpha amino acid residue is derived from natural alpha amino acids such as those listed in the IUPAC-IUB Joint Commision on Biochemical Nomenclature report on the Nomenclature and Symbolism for Amino Acids and Peptides (J. Biol Chem., 260, 14–42 (1985) incorporated by reference). The choice of the particular amino acid residue used in the design of the phosphonate inhibitor will depend on the enzyme targeted for inhibition. For example, with chymotrypsin-like enzymes which prefer Trp, Tyr, or Phe at the $P_1$ position of their substrates, —$Trp^P$—, $Tyr^P$—, and $Phe^P$— residues would be suitable phosphonate residues to incorporate into the $P_1$ position of an inhibitor. With elastase-like enzymes which prefer Val, Ser, or Ala at the $P_1$ position of their substrates, —$Val^P$—, $Ser^P$—, and $Ala^P$— residues would be suitable phosphonate residues to incorporate in the $P_1$ position of an inhibitor. Likewise with trypsin-like enzyme —$Lys^P$— or —$Arg^P$— residues would be suitable.

Unnatural blocked or unblocked alpha amino acid residues can also be used in the design of phosphonate inhibitors. If the target serine protease will hydrolyze a substrate containing the unnatural amino acid residue at the $P_1$ position or if an inhibitor structure contains the unnatural amino acid residue as the $P_1$ residue, then this residue can be used in the design of a phosphonate inhibitor. For example, chymotrypsin hydrolyzes parafluorophenylalanine containing substrates and thus the —HN—CH($CH_2C_6H_4F$)—P(O)— would be suitable for incorporating into a chymotrypsin inhibitor. Likewise, trypsin will hydrolyze substrates with aminoethylcystein residues and cathespin G will hydrolyze aminopropylcystein residues and thus —HN—CH($CH_2SCH_2CH_2NH_2$)—P(O)— and —HN—CH(CH$_2$SCH$_2$CH$_2$NH$_2$)—P(O)— would respectively be suitable residues to incorporate into inhibitors for trypsin and cathepsin G. One skilled in the art of designing inhibitors for proteolytic enzyme can list many other unnatural amino acid residues which could be used in the design of suitable inhibitors.

Other aryl diesters of α-aminoalkylphosphonic acids have been prepared earlier for other purposes (illustrative examples: Oleksyszyn, J. et al., Synthesis, 1979, 985–986.; Vo-Quang, Y. et al., J. Med. Chem. 1986, 43, 579–581.; Kafarski, P. et al., Tetrahedron, 1987, 43, 799–803.; Szewczyk, J. et al., Synthesis, 1982, 409–414; the preceding articles are incorporated herein by reference).

A few other derivatives of α-aminoalkylphosphonic acids have been prepared recently for inhibition of serine proteases, but they are not peptidyl derivatives or are peptidyl derivatives with the phosphonic acid moiety inside the peptide chain (Bartlett et al., Bioorg. Chem., 1986, 14, 356–377, Lamden et al., Biochem. Biophys. Res. Commun., 1983, 112, 1085–1090; the preceding articles are incorporated herein by reference). We have published some of our work in a paper Irreversible Inhibition of Serine Proteases by Peptidyl Derivatives of α-Aminoalkylphosphonate Diphenyl Esters, Oleksyszyn and Powers, *Biochem. Biophys. Res. Commun.* 1989, 161,143–149. Subsequently, Fastrez et al., *Tetrahedron Lett.,* 1989, 30, 6861–6864 reported phosphonate inhibitors similar to those which we reported (both the preceding articles are incorporated herein by reference).

The following compounds are representative of but do not limit the invention:

Diphenyl amino(4-amidinophenyl)methane-phosphonate dihydrochloride
(NH$_2$—CH(Am-C$_6$H$_4$)PO(OPh)$_2$)
Diphenyl N-benzyloxycarbonylamino(4-amidinophenyl) methanephosphonate hydrochloride
(Cbz-NH-CH(Am-C$_6$H$_4$)PO(OPh)$_2$)
Diphenyl N-(N-benzyloxycarbonylprolyl)amino(4-amidinophenyl)methanephosphonate hydrochloride (Cbz-NH-Pro-NHCH(Am-C$_6$H$_4$)PO(OPh)$_2$)
Diphenyl N-(D-Phe-Pro)amino(4-amidinophenyl)methanephosphonate dihydrochloride
(D-Phe-Pro-NH CH(Am-C$_6$H$_4$)PO(OPh)$_2$)
Diphenyl N-(Boc-D-Phe-Pro)amino(4-amidinophenyl) methanephosphonate hydrochloride
(Boc-D-Phe-Pro-NHCH(Am-C$_6$H4)PO(OPh)$_2$)
Diphenyl N-(N-β-napthylsulfonylglycyl)amino(4-amidinophenyl)methanephosphonate hydrochloride (Naphthylsulfonyl-Gly-NHCH(Am-C$_6$H$_4$)PO(OPh)$_2$)
Cbz-Ala$^P$(OCH$_2$CF$_3$)$_2$
Cbz-Phe$^P$(OCH$_2$CF$_3$ )$_2$
Cbz-Val$^P$(4-F-C$_6$H$_4$O)$_2$
Cbz-Met$^P$(OPh)$_2$
Cbz-Met(O)P(OPh)$_2$
Met$^P$(OPh)$_2$.HBr
Cbz-NHCH(4-NO$_2$-C$_6$H$_4$)PO(OPh)$_2$
Benzoyl-NHCH(4-NH$_2$-C$_6$H$_4$)PO(OPh)$_2$
Cbz-NHCH(4-CN-C$_6$H$_4$)PO(OPh)$_2$
NH$_2$CH(4-NO$_2$-C$_6$H$_4$)PO(OPh)$_2$
Cbz-NHCH(CH$_2$=CH—)PO(OPh)$_2$
Cbz-NHCH(4-CO$_2$H-C$_6$H$_4$)PO(OPh)$_2$
Cbz-NHCH(3-CH$_3$-C$_6$H$_4$)PO(OPh)$_2$
CF$_3$CF$_2$CF$_2$CO-Ala$^P$(OPh)$_2$
(m-Tos-Phe)-C$_6$H$_4$CO-Val$^P$(OPh)$_2$
Cbz-Ala-Ala$^P$(OPh)$_2$
Cbz-Ala-Phe$^P$(OPh)$_2$
Cbz-Ala-Val$^P$(OPh)$_2$
Cbz-Pro-Val$^P$(OPh)$_2$
Cbz-Pro-Phe$^P$(OPh)$_2$
Cbz-Phe-Phe$^P$(OPh)$_2$
Cbz-Leu-Phe$^P$(OPh)$_2$
Cbz-Val-Phe$^P$(OPh)$_2$
Cbz-Val-Val$^P$(OPh)$_2$
Cbz-Pro-Val$^P$(4-F-C$_6$H$_4$O)$_2$
Cbz-Pro-Phe$^P$(OCH$_2$CF$_3$)$_2$
Cbz-Pro-Val$^P$(OEt)$_2$
Boc-Pro-Phe$^P$(OPh)$_2$
Boc-Pro-Val$^P$(OPh)$_2$
Boc-Pro-Nva$^P$(OPh)$_2$
Ala-Ala$^P$(OPh)$_2$.HBr
Phe-Ala$^P$(OPh)$_2$.CF$_3$COOH
Cbz-Ala- Ala-Val$^P$(OPh)$_2$
Cbz-Phe-Pro-Phe$^P$(OPh)$_2$
Cbz-Val-Val-Val$^P$(OPh)$_2$
Cbz-Phe-Pro-Phe$^P$(OPh)$_2$
Suc-Phe-Pro-Phe$^P$(OPh)$_2$
Suc-Val-Pro-Phe$^P$(OPh)$_2$
Boc-Val-Pro-Val$^P$(OPh)$_2$
Boc-Ala-Pro-Val$^P$(OPh)$_2$
MeO-Suc-Ala-Ala-Pro-Met$^P$(OPh)$_2$
MeO-Suc-Ala-Ala-Pro-Met(O)$^P$(OPh)$_2$
MeO-Suc-Ala-Ala-Ala-Val$^P$(OPh)$_2$
MeO-Suc-Ala-Ala-Ala-Nva$^P$(OPh)$_2$
MeO-Suc-Ala-Ala-Ala-Phe$^P$(OPh)$_2$
MeO-Suc-Ala-Ala-Pro-Val$^P$(OPh)$_2$
MeO-Suc-Ala-Ala-Pro-Phe$^P$(OPh)$_2$
MeO-Suc-Ala-Ala-Pro-Leu$^P$(OPh)$_2$
MeO-Suc-Ala-Ala-Pro-Nva$^P$(OPh)$_2$
Diphenyl Pyrrolidine-2-phosphonate Hydrochloride (HCl.Pro$^P$(OPh)$_2$)
Diphenyl Piperidine-2-phosphonate Hydrochloride (HCl.Pip$^P$(OPh)$_2$)
Di(4-chlorophenyl)Pyrrolidine-2-phosphonate Hydrochloride (HCl.Pro$^P$(OPh-4-Cl)$_2$)
Di(4-chlorophenyl)Piperidine-2-phosphonate Hydrochloride (HCl.Pip$^P$(OPh-4-Cl)$_2$)
Di(4-fluorophenyl)Piperidine-2-phosphonate Hydrochloride (HCl.Pip$^P$(OPh-4-F)$_2$)
Diphenyl Alanylpyrrolidine-2-phosphonate Hydrochloride (HCl.Ala-Pro$^P$(OPh)$_2$)
Cbz-Ala-Pro$^P$(OPh)$_2$
Ala-Pip$^P$(OPh)$_2$
Ala-Pip$^P$(OH)(OPh)
Cbz-Ala-Pip$^P$(OPh)$_2$
Phe-Pro$^P$(OPh)$_2$
Cbz-Phe-Pro$^P$(OPh)$_2$
Lys-Pro$^P$(OPh)$_2$
Cbz-Lys(Cbz)-Pro$^P$(OPh)$_2$
Lys-Pip$^P$(OPh)$_2$
Cbz-Lys(Cbz)-Pip$^P$(OPh)$_2$
Ala-Pro$^P$(OPh-4-Cl)$_2$
Cbz-Ala-Pro$^P$(OPh-4-Cl)$_2$
Ala-Pip$^P$(OPh-4-Cl)$_2$
Cbz-Ala-Pip$^P$(OPh-4-Cl)$_2$
Ala-Pip$^P$(OPh-4-F)$_2$
Cbz-Ala-Pip$^P$(OPh-4-F)$_2$ It has been found that compounds of the present invention have effective inhibitory activity against DPP-IV as shown in Table I. At inhibitor concentrations of 0.12 mM and with a 2 min incubation time, only Lys-Pip$^P$(OPh)$_2$ (11) and Ala-Pip$^P$(OPh-4-Cl)$_2$ (13) effectively inhibited DPP-IV. With a 30 min incubation time, five dipeptide phosphonates (6, 7, 11, 12, 13) showed some inhibitory potency. The monoester Ala-Pip$^P$(OH)(OPh) (8), compound 9 with Phe at the P$_2$ site and 10 did not show any inhibition of DPP-IV under these conditions.

TABLE I

Inhibition of Human Placenta DPP-IV by Peptidyl Phosphonates[a]

| Inhibitors | [I] (mM) | % Inhibition 2 min | % Inhibition 30 min |
|---|---|---|---|
| 6 HCl.Ala—Pro$^P$(OPh)$_2$ | 0.12 | 0 | 33 |
| 7 AcOH.Ala—Pip$^P$(OPh)$_2$ | 0.12 | 0 | 100 |
| 8 AcOH.Ala—Pip$^P$(OH)(OPh) | 0.12 | 0 | 0 |
| 9 HBr.Phe—Pro$^P$(OPh)$_2$ | 0.12 | 0 | 0 |
| 10 2HBr.Lys—Pro$^P$(OPh)$_2$ | 0.12 | 0 | 0 |
| 11 2HCl.Lys—Pip$^P$(OPh)$_2$ | 0.12 | 35 | 88 |
| 12 HCl.Ala—Pro$^P$(OPh-4Cl)$_2$ | 0.12 | 0 | 100 |
| 13 HCl.Ala-Pip$^P$(OPh-4Cl)$_2$ | 0.12 | 88 | 100 |

[a]Percentage inhibition was measured after 2 or 30 min incubation in 0.05 M Tris, pH 7.8 buffer and 5% Me$_2$SO and at 23° C. TFA.Ala—Pro—AFC (0.190 mM) was used as the substrate.

The second-order inhibition rate constants $k_{obs}/[I]$ for the better inhibitors are shown in Table II. The best inhibitor was Ala-Pip$^P$(OPh-4-Cl)$_2$ (13). Substitution of phenoxy by a 4-chlorophenoxy group improves the inhibition rate by 12–23 fold (12>6; 13>7). However, the inhibition rate of DPP-IV by compound 14 containing a 4-fluorophenyl group is similar to the inhibition rate for the unsubstituted phenoxy derivative 7. Replacing the Pro phosphonate by a homoproline phosphonate (Pip$^P$) also enhanced the inhibition by 2–10 fold (7>6; 11>10; 13>12). Previous studies with synthetic substrates demonstrated that DPP-IV hydrolyzed the dipeptide p-nitroanilides AA-Pro-pNA faster when the $P_2$ site contained a Pro, Abu, Leu, Val, or Ala rather than Phe or Lys. In the Pro or homoproline-containing phosphonate inhibitors, Ala is preferred at the $P_2$ site rather than Lys or Phe. For example, Ala-Pro$^P$(OPh)$_2$ (6) but not Phe-Pro-$^P$(OPh)$_2$ (9) or Lys-Pro$^P$(OPh)$_2$ (10) inhibited DPP-IV at 0.12 mM and 30 min incubation (Table I). Similarly, Ala-Pip$^P$(OPh)$_2$ (11) inhibited DPP-IV more potently than Lys-Pip$^P$(OPh)$_2$ (7). Interestingly, both Pro and homoproline-containing dipeptide phosphonates inhibited DPP-IV and the substitution of a Pro phosphonate by a homoproline phosphonate enhanced the inhibition rates. This indicates that the $S_1$ pocket of DPP-IV is bigger than a proline ring and can accommodate the larger homoproline structure.

TABLE II

Rates of Inhibition of DPP-IV by Peptide Phosphonates and Half-Lives for Hydrolysis of Peptide Phosphonates[a]

| Inhibitors | $t_{1/2}$ (h) | [I] (mM) | $k_{obs}/[I]$ ($M^{-1}s^{-1}$) |
|---|---|---|---|
| 6 HCl.Ala—Pro$^P$(OPh)$_2$ | 23.1 | 0.42 | 1.2 |
| 7 AcOH.Ala—Pip$^P$(Oph)$_2$ | >72 | 0.42 | 12.6 |
| 10 2HBr.Lys—Pro$^P$(OPh)$_2$ | 52 | 0.42 | 1.7 |
| 11 2HCl.Lys—Pip$^P$(Oph)$_2$ | >48 | 0.42 | 4.2 |
| 12 HCl.Ala—Pro$^P$(OPh-4-Cl)$_2$ | 5.3 | 0.42 | 28 |
| 13 HCl.Ala—Pip$^P$(OPh-4-Cl)$_2$ | 67 | 0.042 | 156 |
| 14 HCl.Ala—Pip$^P$(OPh-4-F)$_2$ | >68 | 0.42 | 12 |

[a]Hydrolysis and inhibition were measured in 0.05 M Tris, pH 7.8 buffer and 8% Me$_2$SO and at 23° C. TFA.Ala—Pro—AFC (0.2 mM) was used as the substrate.

The specificity of these dipeptide phosphonates for DPP-IV was examined by measuring inhibition rates with other proteases and esterases. The results were shown in Table III. Three inhibitors Ala-Pro$^P$(OPh)$_2$ (6), Ala-Pro$^P$(OPh-4-Cl)$_2$ (12), and Ala-Pip$^P$ (OPh-4-Cl)$_2$ (13) inhibited DPP-IV but not six other proteases and esterases. Two chlorophenoxy phosphonates 12 and 13 inhibited chymotrypsin very slowly, which is surprising since chymotrypsin does not hydrolyze peptide substrates with Pro at the $P_1$ site. We postulate that one of the two 4-chlorophenoxy groups in inhibitors 12 and 13 is fitting into the large hydrophobic $S_1$ site of chymotrypsin and this result shows in the inhibition rates. With this exception, the inhibitors are highly specific for DPP-IV.

TABLE III

Inhibition of Proteases and Esterases by Dipeptide Phosphonates[a]

| | $k_{obs}/[I]$ ($M^{-1}s^{-1}$) | | |
|---|---|---|---|
| Enzymes | Ala—Pro$^P$(OPh)$_2$ (6) | Ala—Pro$^P$(OPh-4-Cl)$_2$ (12) | Ala—Pip$^P$(OPh-4-Cl)$_2$ (13) |
| Chymotrypsin | NI[b] | 26 | 18 |
| Trypsin | NI | NI | NI |
| HLE | NI | NI | NI |
| PPE | NI | NI | NI |
| Acetylcholinesterase | NI | NI | NI |
| Papain | NI | NI | NI |
| Cathepsin B | NI | NI | NI |

[a]Inhibition was measured in 0.1 M Hepes, 0.5 M NaCl, pH 7.5 buffer (chymotrypsin, PPE, HLE), 0.1 M Hepes, 0.01 M CaCl$_2$, pH 7.5 (trypsin), 0.1 M phosphate, pH 7.5 (acetylcholinesterase), 0.05 M Tris, 2 mM EDTA, 5 mM cysteine, pH 7.5 (papain), or 0.1 M phosphate, 1.33 mM EDTA, 2.7 mM cysteine, pH 6.0 (cathepsin B), 8–9% Me$_2$SO and at 23° C. Substrates were Suc—Phe—Thr—Phe—pNA (0.48 mM) for chymotrypsin, Z—Phe—Gly—Arg—pNA (0.09 mM) for trypsin, MeO—Suc—Ala—Ala—Pro—Val—pNA (0.24 mM) for HLE, Suc—Ala—Ala—Ala—pNA (0.44 mM) for PPE. Inhibitor concentrations were 0.42 mM.
[b]NI, no inhibition after 30 min of incubation of enzyme with inhibitor.

*Spontaneous Hydrolysis of Dipeptide Phosphonates.* Peptide phosphonates are known to be stable in buffer and plasma (Oleksyszyn, J., Powers, J. C., Irreversible Inhibition of Serine Proteases by Peptide Derivatives of (α-Aminoalkyl)phosphonate Diphenyl Esters, *Biochemistry* 1991, 30, 485–493). Half-lives for hydrolysis of seven phosphonates are shown in Table II. These inhibitors are quite stable with half-lives of 5.3 to >72 h. Phosphonates with a 4-chlorophenoxy group hydrolyzed faster than those with phenoxy group or 4-fluorophenoxy group ($t_{1/2}$:6>12; 7, 14>13). Phosphonates with homoproline at the $P_1$ site are more stable than those with Pro ($t_{1/2}$:7>6; 13>12).

*Inhibition Mechanism.* The proposed inhibition mechanism of DPP-IV by the dipeptide phosphonate, Ala-Pip$^P$(OPh)$_2$ (7), is similar to that previously described for other serine proteases (Oleksyszyn, J., Powers, J. C., Irreversible Inhibition of Serine Proteases by Peptide Derivatives of (α-Aminoalkyl)phosphonate Diphenyl Esters, *Biochemistry* 1991, 30, 485–493). It involves the nucleophilic substitution at the phosphorus atom by the active site Ser-195 through a pentavalent intermediate to form a phophonylated enzyme. The leaving group in these dipeptide phosphonates is an electronegative phenoxy or 4-halophenoxy group. The Pro or Pip residue fits into the $S_1$ pocket. The DPP-IV which was inhibited by compounds 6, 7, 12, or 13 was stable and did not regain enzyme activity after 24 h. Excess inhibitors in the inhibited enzyme solution were removed by centrifugation of the diluted enzyme solution twice using Amicon microconcentrators. These results are consistent with the formation of a stable phosphonylated enzyme derivative.

Inactivation rates of serine proteases by aryl diesters of peptidyl derivatives of α-aminoalkylphosphonates were measured by the incubation method. An aliquot of inhibitor (25 or 50 μl) in Me$_2$SO was added to a buffered enzyme solution (0.01–2.3 μM) to initiate the inactivation. Aliquots (50 μl) were withdrawn at various intervals and the residual enzymatic activity was measured. Me$_2$SO concentration in the reaction mixture was 8–12% (v/v). A 0.1M HEPES, 0.01M CaCl$_2$, pH 7.5 buffer was utilized for trypsin and trypsin-like enzymes. A 0.1M HEPES, 0.5M NaCl, pH 7.5, was utilized for the other serine proteases. The inhibitor concentrations are shown in the Tables I, II, and III. Peptide thioesters or peptide nitroanilides with the appropriate sequences were used as substrates for various serine proteases. All peptide thioesters hydrolysis rates were measured with the assay mixture containing 4,4'-dithiodipyridine ($\epsilon_{324}$=19800 M$^{-1}$cm$^{-1}$). Peptide 4-nitroanilide hydrolysis was measured at 410 nm ($\epsilon_{410}$=8800 M$^{-1}$cm$^{-1}$). First order inactivation rate constants (kobs) were obtained from plots of ln $v_t/v_o$ vs time, and the correlation coefficients were greater then 0.98.

*Standard Assay of DPP-IV.* DPP-IV was assayed in 450 µL of 50 mM Tris, pH 7.8, 0.2 mM Ala-Pro-AFC (freshly diluted from a 20 mM stock in DMF), and 5 µL of enzyme solution at 30° C. or in 2 mL of buffer, 0.2 mM Ala-Pro-AFC (diluted from 8 mM stock in Me$_2$SO) at 23° C. Fluorescence was measured at 400 nm excitation and 505 nm emission. One unit of DPP-IV is defined as the amount of enzyme that will hydrolyze 1.0 µmole of Ala-Pro-AFC per min at 25° C. and pH 7.8.

*Enzyme Irreversible Inactivation—Incubation Method.* An aliquot of inhibitor (25 or 50 µL) in Me$_2$SO was added to 0.28–0.55 mL of a buffered enzyme solution (0.83 munits for DPP-IV; 2.1 units for acetylcholinesterase; 0.07–4.5 µM for other enzymes) to initiate the inactivation reaction. Aliquots (20–250 µL) were withdrawn at various intervals and the residual enzymatic activity was measured at 23° C. as described below. The buffers were: 0.05M Tris, pH 7.8 for DPP-IV; 0.1M Hepes, 0.01M CaCl$_2$, pH 7.5 for bovine trypsin; 0.1M Hepes, 0.5M NaCl, pH 7.5 for bovine chymotrypsin, PPE, and HLE; 0.1 M phosphate, pH 7.5 for acetylcholinesterase; 50 mM Tris-HCl, 2 mM EDTA, 5 mM cysteine, (freshly prepared) pH 7.5 buffer for papain and 100 mM KH$_2$PO$_4$, 1.33 mM EDTA, 2.7 mM cysteine (freshly prepared), pH 6.0 buffer for cathepsin B. The Me$_2$SO concentration in the reaction mixtures was 8–9% (v/v). The inhibitor concentrations are shown in the appropriate table. Stock solutions of substrates were prepared in Me$_2$SO and stored at −20° C. DPP-IV was assayed with TFA.Ala-Pro-AFC. Papain and cathepsin B were assayed with Bz-Arg-AMC and Z-Arg-Arg-AMC, respectively. The release of AMC were followed fluorometrically (excitation at 380 nm and emmision at 460 nm for AMC). Acetylcholinesterase was assayed with acetylthiocholine iodide in the presence of DTNB at 412 nm. Trypsin was assayed with Z-Phe-Gly-Arg-pNA.HCl (0.09 mM), chymotrypsin was assayed with Suc-Phe-Thr-Phe-pNA (0.48 mM), PPE and HLE were assayed with Suc-Ala-Ala-Ala-pNA (0.44 mM) and MeO-Suc-Ala-Ala-Pro-Val-pNA (0.24 mM), respectively. Peptide p-nitroanilide hydrolysis was measured at 410 nm ($\epsilon_{410}$=8, 800 M$^{-1}$cm$^{-1}$). Pseudo first-order inactivation rate constants ($k_{obs}$) were obtained from plots of ln $v_t/v_o$ vs time, and the correlation coefficients were greater than 0.98.

*Determination of Half-Lives for Spontaneous Hydrolysis of Inhibitors in Buffer.* An aliquot (40 µL) of the phosphonates (5 mM) in Me$_2$SO and 60 µL of Me$_2$SO were added to 1.9 mL of 0.05M Tris, pH 7.8 buffer such that the inhibitor concentration was 0.1 mM and the Me$_2$SO concentration was 10% v/v. The spontaneous hydrolysis was monitored by following the increase in absorbance at 270 nm for phosphonates with phenoxy groups, at 280 nm for compounds with 4-.chlorophenoxy groups or at 277 nm for the 4-fluorophenoxy derivative. Half-lives were obtained from first-order plots of ln (A$_f$-A$_t$) vs time, where A$_t$ is the absorbance of the mixture at time t, and A$_f$ is the final absorbance of phosphonate monophenyl ester and phenol (or corresponding compounds). This was obtained from the absorbance of the solution which had remained constant for a few hours. All the plots gave correlation coefficients of 0.95 or greater.

*Stability of Inhibited* DPP-IV. DPP-IV was inhibited by compounds 6, 7, 13, and 14 (0.042–0.42 mM) in the pH 7.8 buffer. After incubation for 1 h, no enzyme activity was found for inhibitors 7, 13, and 14, and 30% activity was found for 6. Excess inhibitors was removed from diluted solutions of inactivated enzyme by centrifugation three times at 0° C. for 1 h each in Amicon Centricon-10 microconcentrators following addition of buffer. The enzyme activity of solution was assayed at various intervals as described above.

The activity of some proteases correlate directly with the invasiveness of tumor cells. The tumor invasion can be stopped by treatment with inhibitors of serine proteases. Thus the novel inhibitors showed in Table I, Table II and Table III will be useful for treatment of tumors.

The activity of DPP-IV is thought to be one of the responsible enzymes in organ transplant rejection, in autoimmune diseases, in the pathology of AIDS, and related diseases. Thus the novel inhibitors showed in Table I, Table II and Table III will be useful for controlling the immune system, inhibiting the process of organ transplant rejection, for treatment of AIDS, and related disorders.

For treatment of blood coagulation-related diseases, tumor invasion, inflammation, organ transplant rejection, AIDS, or for controlling the immune system, the compounds of the present invention may be administered orally, topically or parenterally. The term parenteral as used includes subcutaneous injection, intravenous, intramuscular, intrasternal injection or infusion techniques. The pharmaceutical compositions containing the active ingredient may be in the form suitable for oral use, for example as tablets, troches, lozenges, aqueous or oily suspension, dispersible powders or granules, emulsions, hard or soft capsules or syrups or elixirs. Dosage levels of the order to 0.2 mg to 140 mg per kilogram of body weight per day are useful in the treatment of above-indicated conditions (10 mg to 7 gms per patient per day). The amount of active ingredient that may be combined with carrier materials to produce a single dosage form will vary depending upon the host treated and the particular mode of administration.

To use the above inhibitors in vitro, they are dissolved in an organic solvent such as dimethylsulfoxide or ethanol, and are added to an aqueous solution containing serine proteases. The final concentration of organic solvent should be less than 25%. The inhibitors may also be added as solids or in suspension. The serine protease inhibitors of this invention would be useful in a variety of experimental procedures where proteolysis is a significant problem. Inclusion of these inhibitors in radioimmunoassay experiments would result in higher sensitivity. The use of these inhibitors in plasma fractionation procedures would result in higher yields of valuable plasma proteins and would make purification of the proteins easier. The inhibitors disclosed here could be used in cloning experiments utilizing bacterial cultures, yeast, and cell lines. The purified cloned product would be obtained in higher yield.

The following examples are given to illustrate the invention and are not intended to limit it in any manner.

EXAMPLE 1

Diphenyl N-benzyloxycarbonylamino(4-cyanophenyl) methanephosphonate was obtained from 9.75 g of 4-cyanobenzaldehyde, 7.65 g of benzyl carbamate and 13.5 ml of triphenyl phosphite in 20 ml of glacial acetic acid, according to the synthetic procedure described earlier (Oleksyszyn J., Subotkowska L., Mastalerz P., Synthesis, 1979, 985). Yield 70%; mp. 135°–138° C.; Anal. Calcd. for $C_{28}H_{23}O_5N_2P\cdot\frac{1}{2}H_2O$: C, 66.27; H, 4.73; N, 5.52. Found: C, 66.03; H, 4.51; N, 5.49.

Cbz-NHCH(4-NO$_2$-C$_6$H$_4$)PO(OPh)$_2$ and Cbz-NHCH(3-Me-C$_6$H$_4$)PO(OPh)$_2$ with m.p. of 151°–153° C. and 127°–129° C. respectively were obtained by the same procedure using the corresponding benzaldehyde.

Diphenyl N-benzyloxycarbonylamino(4-amidinophenyl)-methanephosphonate hydrochloride. A solution of 7 g diphenyl N-benzyloxycarbonylamino( 4-cyanophenyl)-methanephosphonate in 150 ml of dry chloroform and 15 ml of absolute ethanol was saturated with dry HCl at 0° C. The mixture was kept in the refrigerator until TLC (thin layer chromatography) showed the absence of starting material (about 24 hrs). An excess of pentane was added and the precipitated solid was removed by filtration and dried using a vacuum line. The solid was dissolved in 200 ml of dry methanol and gaseous dry ammonia was passed through the solution (one equivalent is required) for about 20 min. Methanol and excess ammonia was removed quickly on a rotary evaporator. A 100 ml portion of fresh methanol was added and solution was heated at 50° C. for about 8 hrs until the TLC shows the absence of imino ether. The solvent was evaporated and the resulting oil was dissolved in chloroform. Addition of ether caused the oil to solidify. After filtration the resulting solid was again dissolved in chloroform, the solution was filtered and the solid was precipitated by addition of ether. In several experiments, the yields were 70–80%; mp. 154°–158° C. (decomp); $^{31}$P NMR 14.87 ppm. Anal. Calcd. for $C_{28}H_{27}O_5N_3ClP\cdot0.3\ NH_4Cl\cdot H_2O$: C, 57.41; H, 5.16; N, 7.52; Cl, 7.31. Found: C, 57.75; H, 5.00; N, 8.86; Cl, 7.43

EXAMPLE 2

Cbz-Val$^P$(4-F-C$_6$H$_4$O)$_2$. Tris(4-fluorophenyl) phosphite was prepared by a previously described method (Walsh, J. Am. Chem. Soc. 1959, 81, 3023–3031). Cbz-Val$^P$( 4-F-C$_6$H$_4$O)$_2$ was obtained from 6.8 ml of isobutyraldehyde (0.075 mole), 7.65 g benzyl carbamate (0.05 mole) and 18.2 g of tris(4-fluorophenyl) phosphite in 10 ml of glacial acetic acid as described in example 1, mp. 94°–96° C. Anal. Calcd. for $C_{24}H_{24}NO_5PF_2$: C, 60.63; H, 5.05; N, 2.95. Found C, 60.84; H, 5.11; N, 2.90.

Cbz-Ala$^P$(4-Me-C$_6$H$_4$O)$_2$, Cbz-Ala$^P$(4-Cl-C$_6$H$_4$O)$_2$, Cbz-Ala$^P$(3,4-dichloro-C$_6$H$_3$O)$_2$, Cbz-Ala$^P$(4-F-C$_6$H$_4$O)$_2$, Cbz-Val$^P$(4-Me-C$_6$H$_4$O)$_2$, Cbz-Val$^P$ (3,4-dimethyl-C$_6$H$_3$O)$_2$, Cbz-Phe$^P$(4-F-C$_6$H$_3$O)$_2$, Cbz-Phe$^P$(3,4-dimethyl-C$_6$H$_3$O)$_2$ can be prepared by the same procedure using the corresponding tris(substituted-phenyl) phosphite and the corresponding aldehyde.

In general, Cbz-NH-CH(R)-P(O)(OZ)(OZ$^1$) can be prepared by reaction of R—CHO with P(OZ)(OZ$^1$)(OZ$^2$).

EXAMPLE 3

Diphenyl amino(4-amidinophenyl)methanephosphonate dihydrochloride. A sample of 1.8 g of diphenyl N-benzyloxycarbonylamino(4-amidinophenyl)methanephosphonate hydrochloride was dissolved in 150 ml of 2N HCl methanol solution and after addition of 5% Pd/C catalyst, the solution was stirred under an atmosphere of hydrogen until the theoretical amount of hydrogen was consumed. The catalyst was removed by filtration and after evaporation of the methanol, the residue was crystallized from ethanol-ether. In several experiments, the yields were 60–80%; mp. 213°–215° C.; Anal. Calcd. for $C_{20}H_{22}N_3ClP\cdot\frac{1}{2}H_2O$: C$_{,51.85}$; H, 4.97; N, 9.08; Cl, 15.34. Found: C, 51.73; H, 5.02; N, 9.10; Cl, 15.36.

Ala$^P$(4-F-C$_6$H$_4$O)$_2$.HCl, Val$^P$(4-Me-C$_6$H$_4$O)$_2$.HCl, Phe$^P$(4-Cl-C$_6$H$_4$O)$_2$.HCl can be prepared by the same procedure.

In general, NH$_2$-CH(R)-P(O)(OZ)(OZ$^1$) hydrochloride can be prepared from Cbz-NH-CH(R)-P(O)(OZ)(OZ$^1$) using the same procedure. This intermediate can then be used to prepare a great variety of derivatives by reaction with acylating agents, carbamylating agents, sulfonylating agents, chloroformates, or by coupling with a variety of peptides and blocked peptides using standing peptide coupling reactions, many of which are illustrated in the following examples.

Diphenyl N-(N-benzyloxycarbonylprolyl)amino(4-amidinophenyl)methanephosphonate hydrochloride. To 0.5 g (2 mmol) of N-benzyloxycarbonylproline in 3 ml of dry DMF at 0° C., 0.45 g (2.77 mmol) of CDI was added and the reaction mixture was stirred at 0° C. for 1 hr. Then 0.9 g (2 mmol) of diphenyl amino(4-amidinophenyl)methanephosphonate hydrochloride was added. After stirring by 18 hrs at 0°–5° C., 10 ml of water was added. The oil which precipitated was washed with water and solidified by washing with a cold 0.1N solution of HCl. One gram of compound was obtained which was used without purification in the next step. $^{31}$P NMR 12.31, 12.62 (free base) and 15.11, 15.41 ppm (hydrochloride). After addition of one drop concentrated HCl to the NMR tube, 14.22, 14.54 ppm (ratio 1:1).

Benzoyl-Ala-Val$^P$(OPh)$_2$, Formyl-Ala-Val$^P$(OPh)$_2$, Fmoc-Ala-Val$^P$(OPh)2 [Fmoc, 9-fluorenylmethyloxycarbonyl], PhNHCO-Ala-Val$^P$(OPh)$_2$, PhNHCS-Ala-Val$^P$(OPh)$_2$, Dansyl-Ala-Val$^P$(OPh)$_2$, Tosyl-Ala-Val$^P$(OPh)$_2$, Trityl-Ala-Val$^P$(OPh)$_2$, Phthaloyl-Ala-Val$^P$(OPh)$_2$, Cbz-Pro-Ala$^P$(4-F-C$_6$H$_4$O)$_2$, Cbz-Pro-Val$^P$ (4-Me-C$_6$H$_4$O)$_2$, Cbz-Pro-Val$^P$(3-Cl-C$_6$H$_4$O)$_2$, Cbz-Pro-Phe$^P$(4-Cl-C$_6$H$_4$O)$_2$, Cbz-Pro-Phe$^P$(4-F-C$_6$H$_4$O)$_2$, Cbz-Ala-Val$^P$(3-Me-C$_6$H$_4$O)$_2$, Cbz-Ala-Phe$^P$(3,4-dichloro-C$_6$H$_3$O)$_2$ can be prepared by the same procedure by coupling with the appropriate blocked amino acid or amino acid derivative.

EXAMPLE 4

Diphenyl N-(D-Phe-Pro)amino(4-amidinophenyl)methanephosphonate dihydrochloride. One gram of derivative obtained in the previous experiment was hydrogenated in 1N solution of HCl in methanol with 0.1 g 5% Pd/C, until the theoretical amount of hydrogen was consumed. After filtration of the catalyst and evaporation of the solvent, the resulting oil was dried using a vacuum linc. A 0.9 g ( 1.64 mmol) sample of the product dihydrochloridc was added to a solution of 0.43 g ( 1.64 mmol) of Boc-D-Phe and 0.34 g (2 mmol) of DCI in 2 ml dry DMF, which was allowed to react for 1 hrs at 0° C. After 24 hrs 10 ml of water was added and the oil which precipitated was decanted. After washing with 0.1N HCl, the oil which solidified was separated by filtration and dried using a vacuum linc. The dry solid was dissolved in 1N HCl solution in methanol and solution was stirred by 1 hr. Solvent was removed on a rotary evaporator and the oil was dried using a vacuum line by several hours to give 0.3 g of product. Yield 24%; mp. 220°–224° C.; $^{31}$P NMR, 16.95, 17.25, 17,60 ppm (stercoisomcrs and conformers). Anal. Calcd. for $C_{34}H_{38}O_5N_2ClP\cdot5H_2O$: C, 51.78; H, 6.09; N, 8.88; Cl, 9.00; Found; C, 51.21; H, 5.95; N, 9.04; Cl, 8.97.

EXAMPLE 5

Diphenyl N-(Boc-D-Phe-Pro)amino(4-amidinophenyl) methanephosphonate hydrochloride. To 0.36 g (1.0 mmol)

of Boc-D-Phe-Pro-OH in 2 ml of dry DMF at 0° C., 0.17 g (1.05 mmol) of CDI was added. After stirring for 1 hr at 0° C., 0.45 g (1.0 mmol) of dihydrochloride of diphenyl amino(4-amidinophenyl)methanephosphonate was added and the solution was stirred for 48 hrs at 0° C. Water (10 ml) was added and the oil which precipitated out was decanted and washed with distilled water. The oil was dissolved in chloroform and the solution was washed with 4% $NaHCO_3$, water, and 0.05N HCl. After drying over $MgSO_4$, the solvent was removed and the resulting oil was dried on a vacuum line for a few hours to give 0.22 g of product. Yield 29%; mp. 185°–190° C.; $^{31}P$ NMR, 12.42, 12.66, 12.79 ppm (stereoisomers and conformers) (free base); 15.12, 15.38, 15.58 (hydrochloride). Anal. Calcd. for $C_{39}H_{45}O_7N_5ClP.\frac{1}{2}H_2O$: C, 60.75; H, 5.97; N, 9.08; Cl, 4.60. Found: C, 60.98; H, 6.48; N, 8.26; Cl., 4.26.

Tosyl-D-Phe-Pro-Arg$^P$(OPh)$_2$, Cbz-D-Phe-Pro-Arg-$^P$(OPh)$_2$, Boc-D-Phe-Pro-Arg$^P$(OPh)$_2$, Boc-D-Phe-Pro-Orn$^P$(OPh)$_2$, Boc-D-Phe-Pro-Arg$^P$(4-F-$C_6H_4O$)$_2$, Boc-D-Phe-Pro-Arg$^P$ (4-Me-$C_6H_4O$)$_2$, Boc-D-Phe-Pro-Arg$^P$(3,4-dichloro-$C_6H_3O$)$_2$, Boc-D-Phe-Pro-Arg$^P$ (3-Cl-$C_6H_4O$)$_2$ can be prepared by the same procedure by coupling with the appropriate blocked peptide or peptide derivative.

EXAMPLE 6

Diphenyl N-(N-β-naphylsulfonylglycyl)amino(4-amidinophenyl)methanephosphonate hydrochloride. Using the same procedure as example 5, 0.3 g (1.13 mmol) of β-naphylsulfonylglycine, 0.2 g (1.23 mmol) of CDI and 0.45 g (1.0 mmol) of diphenyl amino(4-amidinophenyl)methanephosphonate dihydrochloride (obtained in Example 3) were reacted and 0.21 g of product was obtained. Yield 30%; mp. 205°–210° C. (decomp); $^{31}P$ NMR, 11.76 ppm (free base), 14.74 ppm (hydrochloride). Anal. Calcd. for $C_{32}H_{30}O_6N_4ClPS.H_2O$: C, 56.24; H, 4.69; N, 8.20; S, 4.69. Found: C, 56.87; H, 4.43; N, 8.79; S, 5.06.

EXAMPLE 7

Cbz-Met$^P$(OPh)$_2$. This compound was synthesized by the method described in Example 1: yield 36%; mp. 93°–95° C.; one spot on TLC, $R_f$=0.73; $^{31}P$ NMR 19.68 ppm. Anal. Calcd. for $C_{24}H_{26}O_5NSP$: C, 61.15; H, 5.52; N, 2.97; S, 6.79. Found: C, 61.06; H, 5.60; N, 2.91; S, 6.88.

Cbz-Met$^P$(4-Cl-$C_6H_4O$)$_2$, Cbz-Met$^P$(4-Me-$C_6H_4O$)$_2$, Cbz-Met$^P$(3-Me-$C_6H_4O$)$_2$, Cbz-Met$^P$(4-F-$C_6H_4O$)$_2$, Cbz-Met$^P$(3,4-dimethyl-$C_6H_3O$)$_2$ by the same procedure using corresponding tris(substituted phenyl) phosphite.

MeO-Suc-Ala-Ala-Pro-Met$^P$(OPh)$_2$. The reaction of MeO-Suc-Ala-Ala-Pro-OH (0.64 g, 1.73 mmol), $H_2N$-$CH(CH_2CH_2SCH_3)P(O)(Oph)_2$.HBr (0.85 g, 2 mmol), obtained from Cbz-Met$^P$(OPh)$_2$, N-methylmorpholine (0.2 ml, 2 mmol) and DCC (0.34 g, 1.73 mmol) under an atmosphere of nitrogen gave 0.5 g (42%) of product as white solid. A 0.2 g sample was purified on preparative TLC under an atmosphere of nitrogen to give product as a white solid: mp. 41°–43° C.; one spot on TLC, $R_f$=0.6; $^{31}P$ NMR 19.50, 19.36 ppm, ratio 1:1.32. Anal. Calcd. for $C_{32}H_{43}O_9N_4PS.THF$; C, 56.69; H, 6.69; N, 7.35; S, 4.20. Found: C, 57.37; H, 6.77; N, 7.76; S, 4.49.

MeO-Suc-Ala-Ala-Pro-Met$^P$(4-Cl-$C_6H_4O$)$_2$, MeO-Suc-Ala-Ala-Pro-Met$^P$ (3-Me-$C_6H_4O$)$_2$, MeO-Suc-Ala-Ala-Pro-Met$^P$(3,4-dimethyl-$C_6H_3O$)$_2$ can be prepared by the same procedure.

EXAMPLE 8

Cbz-Ala-Ala-Val$^P$(OPh)$_2$. Cbz-Ala-Ala-OH (0.294 g, 1 mmol) was dissolved in 10 ml of dry THF and cooled to 0° C. Diphenyl α-amino-2-methylpropylphosphonate, (0.305 g, 1 mmol) and DCC (0.203 g, 1 mmol) were added to this solution. After stirring for 8 hrs at 0° C. and overnight at room temperature, the solution was worked-up as described above. Recrystallization from chloroform-pentane gave 0.182 g (31%) of crude product. A sample (0.1 g) was purified on preparative thin layer chromatography using chloroform-methanol (9:1) as eluent. The product was recrystallized from ethanol-pentane to give a white solid: mp. 93°–97° C.; one spot on TLC, $R_f$=0.71; $^{31}P$ NMR 19.44, 19.31 ppm, ratio 1:1.11. Anal. Calcd. for $C_{30}H_{36}O_7N_3P.EtOH$; C, 61.19; H, 6.69; N, 6.69. Found: C, 61.32; H, 6.48; N, 6.91.

Cbz-Ala-Ala-Val$^P$(4-Cl-$C_6H_4O$)$_2$, Cbz-Ala-Ala-Val$^P$(4-OMe-$C_6H_4O$)$_2$, Cbz-Ala-Ala-Val$^P$(4-F-$C_6H_4O$)$_2$, Cbz-Ala-Ala-Phe$^P$(3,4-dimethyl-$C_6H_3O$)$_2$, Cbz-Ala-Ala-Nva$^P$(3,4-dichloro-$C_6H_3O$)$_2$, Cbz-Ala-Ala-Met$^P$(4-Cl-$C_6H_4O$)$_2$, Acetyl-Ala-AlaVal$^P$(OPh)$_2$, $CF_3$-CO-Ala-Ala-Val$^P$(OPh)$_2$, Dansyl-Ala-Ala-Val$^P$(OPh)$_2$, Tosyl-Ala-Ala-Val$^P$(OPh)$_2$, Fmoc-Ala-Ala-Val$^P$(OPh)$_2$, PhNHCO-Ala-Ala-Val$^P$(OPh)$_2$ can be prepared by the same procedure by coupling with the appropriate blocked peptide or peptide derivative.

EXAMPLE 9

MeO-Suc-Ala-Ala-Ala-Nva$^P$(OPh)$_2$. The reaction of 0.345 g (1 mmol) of MeO-Suc-Ala-Ala-Ala-OH and 0.305 g (1 mmol) of diphenyl α-aminobutylphosphonate gave 0.35 g (55.3%) of product as a white solid. A 0.1 g sample was purified on preparative TLC as described above to give the product as white solid: top. 215°–218 ° C.; one spot on TLC, $R_f$=0.73; $^{31}P$ NMR 20.02 ppm. Anal. Calcd. for $C_{30}H_{41}O_9N_4P$: C, 56.96; H, 6.49; N, 8.86. Found: C, 56.72; H, 6.58; N, 8.80.

Acetyl-Ala-Ala-Ala-Nva$^P$(OPh)$_2$, Boc-Ala-Ala-Ala-Nva$^P$(OPh)$_2$, MeO-Suc-Ala-Ala-Ala-Nva$^P$ (4-Cl-$C_6H_4O$)$_2$, MeO-Suc-Ala-Ala-Ala-Nva$^P$(3,4-dimethyl-$C_6H_3O$)$_2$, MeO-Suc-Ala-Ala-Ala-Nva$^P$(4-F-$C_6H_4O$)$_2$, MeO-Suc-Ala-Ala-Ala-Nva$_P$(3-Cl-$C_6H_4O$) $_2$ can be prepared by the same procedure using the corresponding tripeptide and diester ofα-aminobutylphosphonate.

EXAMPLE 10

MeO-Suc-Ala-Ala-Ala-Val$^P$(OPh)$_2$. The reaction of MeO-Suc-Ala-Ala-Ala-OH (0.345 g, 1 mmol) and diphenyl α-amino-2-methylpropylphosphonate (0.305 g, 1 mmol) gave 0.3 g (47.5%)of product as white solid. A 0.1 g sample was purified on preparative TLC as described above to give the product as a white solid, which was then recrystallized from ethanol-hexane: mp. 197°–200° C.; one spot on TLC, $R_f$=0.63; $^{31}P$ NMR 19.40, 19.24 ppm, ratio 1:0.72. Anal. Calcd. for $C_{30}H_{41}O_9N_4P.0.25$ Hexane: C, 57.60; H, 6.85; N, 8.61. Found: C, 57.58; H, 6.62; N, 8.36.

Cbz-Ala-Ala-Ala-Val$^P$(OPh)$_2$, MeO-Suc-Ala-Ala-Ala-Val$^P$(4-F-$C_6H_4O$)$_2$, $CH_3$NHCO-Ala-Ala-Ala-Val$^P$(OPh)$_2$, PhNHCS-Ala-Ala-Ala-Val$^P$(OPh)$_2$, MeO-Suc-Ala- Ala-Ala-Val$^P$ (3-Cl-$C_6H_4O$)$_2$, PhNHCO-Ala-Ala-Ala-Val$^P$(3,4-dimethyl-$C_6H_3O$)$_2$, MeO-Suc-Ala-Ala-Ala-Val$^P$ (4-MeO-$C_6H_4O$)$_2$ can be prepared by the same procedure using the corresponding tripeptide and diester of α-amino-2-methylpropylphosphonate.

EXAMPLE 11

MeO-Suc-Ala-Ala-Ala-Phe$^P$(OPh)$_2$. The reaction of MeO-Suc-Ala-Ala-Ala-OH (0.345 g, 1 mmol) and diphenyl α-amino-2-phenyl-ethylphosphonate (0.353 g, 1 mmol) gave 0.35 g (49.1%) of the product which was purified on the preparative TLC, as described above. Recrystallization from methanol gave a whim solid: mp. 207°–210° C.; one spot on TLC, R$_f$=0.69; $^{31}$P NMR 19.06, 19.01 ppm, ratio 1:0.87. Anal. Calcd. for C$_{34}$H$_{41}$O$_9$N$_4$P.MeOH: C, 58.98; H, 6.32; N, 7.86. Found: C, 58.66; H, 6.08; N, 7.96.

MeO-Suc-Ala-Ala-Ala-Phe$^P$(4-Cl-C$_6$H$_4$O)$_2$, MeO-Suc-Ala-Ala-Ala-Phe$^P$ (4-MeO-C$_6$H$_4$O)$_2$ can be prepared by the same procedure.

EXAMPLE 12

MeO-Suc-Ala-Ala-Pro-Val$^P$(OPh)$_2$. MeO-Suc-Ala-Ala-Pro-OH(0.37 g, 1 mmol) was dissolved in 20 ml of dry THF and cooled to 0° C. Diphenyl α-amino-2-methylpropylphosphonate (0.305 g, 1 mmol) and DCC (0.203 g, 1 mmol) were added to this solution. After stirring for 6 hrs at 0° C. and overnight at room temperature, the solution was filtered and 100 ml of ethyl acetate was added. The solution was then washed with 10% citric acid, 4% sodium bicarbonate and water successively. After drying over magnesium sulfate, the solution was filtered, evaporated and the residue was dissolved in 10 ml of THF. Trace of DCU was removed by filtration and after addition of 3 ml of hexane, the solution was allowed to crystallized. After a few days the product was removed by filtration and recrystallized from THF-hexane to give 0.2 g (30%) of a white solid, mp. 83°–86° C.; one spot on TLC, R$_f$=0.74; 31p NMR 19.78, 19.60 ppm, ratio 1:2.12. Anal. Calcd. for C$_{32}$H$_{43}$O$_9$P.hexane: C, 61.30; H, 7.66; N, 7.53. Found: C, 61.04; H, 7.58; N, 7.69.

PhNHCO-Ala-Ala-Pro-Val$^P$(3-Cl-C$_6$H$_4$O)$_2$, PhNHCS-Ala-Ala-Pro-Val$^P$(4-Cl-C$_6$H$_4$O)$_2$, MeO-Suc-Ala-Ala-Pro-Val$^P$(4-Me-C$_6$H$_4$O)$_2$ can be prepared by the same procedure.

EXAMPLE 13

MeO-Suc-Ala-Ala-Pro-Leu$^P$(OPh)$_2$. The reaction of MeO-Suc-Ala-Ala-Pro-OH (0.37 g, 1 mmol) and diphenyl α-amino-3-methylbutylphosphonate (0.32 g, 1 mmol) gave 0.38 g (50.1%) of product as white solid: mp. 60°–64° C.; one spot on TLC, R$_f$ =0.67; $^{31}$P NMR 20.71, 20.54 ppm, ratio 1:1.33. Anal. Calcd. for C$_{33}$H$_{45}$O$_9$N$_4$P.hexane: C, 61.74; H, 7.78; N, 7.38. Found: C, 61.04; H, 7.53; N, 7.59.

EXAMPLE 14

MeO-Suc-Ala-Ala-Pro-Phe$^P$(OPh)$_2$. The reaction of MeO-Suc-Ala-Ala-Pro-OH (0.37 g, 1 mmol) and diphenyl α-amino-2-phenylethylphosphonate (0.35 g, 1 mmol) gave 0.4 g (50.5%) of product as a white solid: top. 53°–56° C.; one spot on TLC, R$_f$=0.7; $^{31}$P NMR 19.41, 19.10 ppm, ratio 1:2.47. Anal. Calcd. for C$_{36}$H$_{43}$O$_9$N$_4$P.hexane: C, 63.62; H, 7.19; N, 7.07. Found: C, 63.42; H, 7.19; N, 7.57.

EXAMPLE 15

Cbz-Pro-Val$^P$(OPh)$_2$. Cbz-Pro-OH (0.97 g, 4 mmol) was dissolved in 40 ml of dry THF and cooled to 0° C. Diphenyl α-amino-2-methylpropylphosphonate (1.2 g, 4 mmol) and DCC (0.81 g, 4 mmol) were added to this solution. After stirring for 6 hrs at 0° C. and overnight at room temperature, the DCU was removed by filtration and 50 ml of ethyl acetate was added. The solution was washed successively twice each time with 10% citric acid, water, 4% sodium bicarbonate and water. After drying over MgSO$_4$, the mixture was filtered, evaporated and residue was dissolved in 10 ml of methylene chloride. A trace of DCU was removed by filtration and after addition of 30 ml of pentane, the solution was allowed to crystallize. After a few days the product was filtered and recrystallized from methylene chloride-hexane to give 1.4 g (65%) of a white solid: mp. 123°–127° C.; one spot on TLC, R$_f$=0.74; $^{31}$P NMR 19.52(broad), 19.51(broad) ppm. Anal. Calcd. for C$_{29}$H$_{33}$O$_6$N$_2$P: C, 64.87; H, 6.15; N, 5.22. Found: C, 64.58; H, 6.23; N, 5.34.

Boc-Val-Pro-Val$^P$(OPh)$_2$. A solution 0.536 g (1 mmol) of Cbz-Pro-Val$^P$(OPh)$_2$ in 50 ml of methanol with 0.1 g 5% Pd/C was stirred under atmosphere of hydrogen at room temperature for 2 hrs and filtered through celite. After addition of of Boc-Val-OH(0.217 g, 1 mmol) to the filtrate, the solvent was removed in vacuo. The residue was dissolved in 20 ml of dry THF and 0.2 g of DCC (1 mmol) was added. The solution was kept at 0° C. for 6 hrs and overnight at room temperature. DCU was removed by filtration and the organic layer was washed with water, twice with 4% NaHCO$_3$, water, twice with 10% citric acid and water. After drying over sodium sulfate, the solvent was evaporated and the resulting oil was dried at low pressure for a few hours to give 0.45 g (72%) of a white hydroscopic solid: mp. 62°–66° C.; one spot on TLC, R$_f$=0.78; $^{31}$P NMR 19.64 ppm. Anal. Calcd. for C$_{31}$H$_{44}$O$_7$N$_3$P.H$_2$O: C, 60.10; H, 7.43. Found: C, 60.26; H, 7.49.

Boc-Val-Pro-Val$^P$(4-F-C$_6$H$_4$O)$_2$, PhNHCS-Val-Pro-Val$^P$(3-Cl-C$_6$H$_4$O)$_2$, ε-Cbz-α-Cbz-Orn-Val-Pro-Val$^P$(4-F-C$_6$H$_4$O)$_2$, Boc-Val-Pro-Val$^P$(4-MeO-C$_6$H$_4$O)$_2$, Tosyl-Val-Pro-Val$^P$(OPh)$_2$ can be prepared by the same procedure.

EXAMPLE 16

Cbz-Pro-PheP(OPh)$_2$. The reaction of Cbz-Pro-OH (0.75 g, 3 mmol), diphenyl α-amino-2-phenylethylphosphonates (1.05 g, 3 mmol) and DCC (0.61 g, 3 mmol) gave 0.93 g (53%) of product as white solid: mp. 81°–84° C.; one spot on TLC, R$_f$=0.74; $^{31}$P NMR 19.54, 19.48, 19,27 and 19.22 ppm (diastereomers and conformers), ratio of diastereomers 1:1. Anal. Calcd. for C$_{33}$H$_{33}$O$_6$N$_2$P: C, 67.81; H, 5.65; N, 4.79. Found: C, 67.56; H, 5.79; N, 4.72.

Cbz-Phe-Pro-Phe$^P$(OPh)$_2$. The reaction of Cbz-Phe-OH (0.3 g, 1 mmol) with the hydrogenolysis product of Cbz-Pro-Phe$^P$(OPh)$_2$ (0.58 g, 1 mmol) and DCC (0.2 g, 1 mmol), gave 0.4 g (54%) of a hydroscopic semi-solid product after a standard workup. A 0.2 g sample was purified on preparative TLC to give the product as a hydroscopic semi-solid: one spot on TLC, Rf=0.76; $^{31}$P NMR 19.67, 19.57, 19.32, 19.19 and 19.07 ppm (diastereomers and conformers); ratio, 1.0:0.34:0.82:0.73:0.92. Anal. Calcd. for C$_{42}$H$_{42}$O$_7$N$_3$P.2H$_2$O: C, 65.71; H, 5.99; N, 5.47. Found: C, 65.62; H, 6.12; N, 5.27.

EXAMPLE 17

Suc-Val-Pro-Phe$^P$(OPh)$_2$. The reaction of Cbz-Val-OH (0.25 g, 1 mmol), DCC (0.2 g, 1 mmol) and the product of hydrogenolysis of Cbz-Pro-Phe$^P$(OPh)$_2$ (0.584 g, 1 mmol) gave an oil which was dissolved in 30 ml of ethyl acetate. To this solution, 0.1 g (1 mmol) of succinic anhydride and 0.1 g of 5% Pd/C were added and mixture was stirred under atmosphere of hydrogen until the TLC showed only one new spot. Catalyst was removed by filtration and organic layer was washed several times with water. After drying, the organic solvent was removed to give 0.45 g (65%) of product as a hydroscopic solid: mp. 50°–53° C.; one spot on TLC, $R_f$=0.4; $^{31}$P NMR 19.75, 19.23 ppm, ratio 1:1. Anal. Calcd. for $C_{34}H_{40}O_3N_3P \cdot 2H_2O$: C, 59.56; H, 6.42. Found: C, 59.59; H, 6.42.

Suc-Val-Pro-Phe$^P$(4-MeS-$C_6H_4O)_2$, Suc-Val-Pro-Phe$^P$(4-Cl-$C_6H_4O)_2$, Suc-Phe-Pro-Phe$^P$(OPh)$_2$, Suc-Val-Pro-Phe$^P$(3-F-$C_6H_4O)_2$, Suc-Val-Pro-Phe$^P$ (3,4,5-trichloro-$C_6H_2O)_2$, Suc-Val-Pro-Phe$^P$(2,3,4-fluoro-$C_6H_2O)_2$, Suc-Val-Pro-Phe$^P$ (4-Me-$C_6H_4O)_2$, Acetyl-Val-Pro-Phe$^P$(OPh)$_2$, $CF_3$-CO-Val-Pro-Phe$^P$(OPh)$_2$ can be prepared by the same procedure.

EXAMPLE 18

Cbz-Ala$^P$(OCH$_2$CF$_3$)$_2$. This compound was obtained by a previously described method involving transesterification (Szewczyk et al., Synthesis, 1982, 409–414). 10 ml of trifluoroethanol and 0.46 g of Na (0.02 mole) were mixed first, then 4.11 g of Cbz-AlaP(OPh)$_2$ was added, and the mixture was stirred overnight. 3 ml of AcOH was added and the solvent was everaporated. The residue was dissolved in CHCl$_3$ and washed with water, 2N NaOH and water, and dried over MgSO$_4$. The solvent was evaporated and the oil was obtained, mass spectrum m/e=423 (M$^+$).

Cbz-Phe$^P$(OCH$_2$CF$_3$)$_2$ was prepared by the same procedure, mp. 85°–87° C., mass spectrum m/e=499 (M$^+$). Cbz-Val$^P$(OCH$_2$CH$_3$)$_2$ was also prepared by the same procedure using ethanol instead of trifuoroethanol.

EXAMPLE 19

Benzoyl-NHCH(4-NH$_2$-C$_6$H$_4$)PO(OPh)$_2$. NH$_2$CH(4-NO$_2$-C$_6$H$_4$)PO(OPh)$_2$·HBr was obtained by deblocking Cbz-NHCH (4-NO$_2$-C$_6$H$_4$)PO(OPh)$_2$ with 30% of HBr/HOAc, mp. 198°–200° C. The reaction of NH$_2$CH(4-NO$_2$-C$_6$H$_4$)PO(OPh)$_2$. HBr and benzoyl chloride in the presence of N-methylmorpholine gave benzoyl-NHCH(4-NO$_2$-C$_6$H$_4$)PO(OPh)$_2$, mp. 157°–159° C., mass spectrum m/e= 489 (M$^+$+1). Anal. Calc. for $C_{26}H_{21}N_2O_6P$: C, 63.88; H, 4.30; N, 5.73. Found: C, 64.05; H, 4.25; N, 5.69. Hydrogenolysis of benzoyl-NHCH(4-NO$_2$-C$_6$H$_4$)PO(OPh)$_2$ in the presence of Pd/C catalyst gave the final product, mp. 156°–158° C., mass spectrum m/e =458 (M$^+$). Anal. Calc. for $C_{26}H_{23}N_2O_4P$: C, 68.12; H, 5.02; N, 6.11. Found: C, 66.87; H, 5.15; N, 5.01.

GENERAL SYNTHESIS PROCEDURES

Benzyl carbamate, diphenyl phosphite, pyrrolidine, piperidine, DCC, and all common chemicals were obtained from Aldrich Co., Milwaukee, Wis. Benzyloxycarbonylproline (Cbz-Pro) and $N^\alpha,N^\epsilon$-dibenzyloxycarbonyllysine were obtained from Bachem Fine Chemicals, Calif. The purity of each new synthesized compound was checked by TLC, $^1$H-NMR, mass spectroscopy (FAB), and elemental analysis. In the case of multi-step synthesis the first and final products were checked by $^1$H-NMR, FAB spectra and elemental analysis. The solvent system used for TLC was chloroform-acetone (9:1 ). Preparative thin-layer chromatography was performed with plates precoated with silica gel (Merck). The NMR spectra were recorded on a Varian Gemini 300 MHz instrument in CDCl$_3$, DMSO-d$_6$, or D$_2$O solutions. Mass spectra (FAB) were recorded on a Vafion MAT Model 112S mass spectrometer. Elemental analysis were performed by Atlantic MicroLab Inc., Norcross, Ga.

Di(4-chlorophenyl) phosphite and di(4-fluorophenyl) phosphite were prepared from tris(4-chlorophenyl) phosphite and tris(4-fluorophenyl) phosphite, respectively using a previously described procedure (Walsh, E. N., Conversion of Tertiary Phosphites to Secondary Phosphonates. Diphenyl Phosphonate, J. Am. Chem. Soc. 1959, 81, 3023–6). Tris(4-chlorophenyl) phosphite was prepared from 4-chlorophenol and phosphorous trichloride with three equivalents of triethyl amine as a base using a modification of a previous procedure (McCombie, H., Saunders, B. C., Stacey, G. J., Esters Containing Phosphorus. Part I, J. Chem. Soc. 1945, 381). Similarly, tris(4-fluorophenyl) phosphite was prepared from 4-fluorophenol and phosphorous trichloride using one equivalent of triethyl amine as a base.

EXAMPLE 20

Diphenyl Pyrrolidine-2-phosphonate Hydrochloride (HCl.Pro$^P$(OPh)$_2$, 1). This compound was synthesized from 1-pyrroline trimer (Nomura, Y., Ogawa, K., Takeuchi, Y., Tomoda, S., One Step Synthesis and Structural Confirmation with 1-Pyrroline Trimer, Chem. Lett. 1977, 693–696) and diphenyl phosphite using the procedure previously described for the synthesis of the diethyl ester (Petrillo, E. W., Spitzmiller, E. R., Synthesis of 2-Phosphopyrrolidine and Its Substitution for Proline in an Inhibitor of Angiotensin-Converting Enzyme, Tet. Lett. 1979, 51, 4929). A mixture of 1-pyrroline trimer (17 mmol, 3.5 g) and diphenyl phosphite (50 mmol, 11.7 g) was heated at 85° C. for 1.5 h under argon to give crude diphenyl pyrrolidine-2-phosphonate which was dissolved in 100 ml of dry diethyl ether, filtered and saturated with dry gaseous HCl. The precipitated hydrochloride 1 was collected by filtration, washed with ether and recrystallized from acetone, to give the pure product as a white solid in 49% yield: mp 146°–148° C.; $^1$H-NMR (D$_2$O) δ(ppm): 2.0–2.5 (m, 4H), 3.40 (m, 2H), 4.25 (m, 1H), 6.90–7.30 (m, 10H); MS (FAB) m/e 304 (M–Cl)[30]. Anal. ($C_{16}H_{19}NO_3PCl$): C, H, N, Cl.

EXAMPLE 21

Diphenyl Piperidine-2-phosphonate Hydrochloride (HCl.Pip$^P$(OPh)$_2$, 2). This compound was prepared from the trimer of 2,3,4,5-tetrahydropyridine and diphenyl phosphite using the procedure previously described for the synthesis of the diethyl ester (Solodenko, V. A., Kukhar, V. P., Synthesis of DL-(2-Piperidyl) Phosphonic Acid, Zh. Obsh. Khim. 1987, 57, 2392). A mixture of the trimer (10 mmol, 2.5 g) and diphenyl phosphite (30 mmol, 7.0 g) was heated for 1.5 h at 100° C. under argon. The resulted crude diphenyl piperidine-2-phosphonate was dissolved in 100 mL of dry ether, undisolved material was removed by filtration, and the solution was saturated with gaseous HCl. The precipitated hydrochloride 2 was collected by filtration, washed with ether, dried and recrystallized from acetone to give a white solid in 41% yield: top. 172°–174° C.; $^1$H-NMR (D$_2$O), δ (ppm) 1.5–2.4 (m, 6H), 3.05 (m, 1H), 3.45 (m, 1H), 4.10 (m, 1H), 6.9–7.4 (m, 10H); MS (FAB) m/e 318 (M–Cl)$^+$. Anal. ($C_{17}H_{21}NO_3PCl$): C, H, N, Cl.

EXAMPLE 22

Di(4-chlorophenyl) Pyrrolidine-2-phosphonate Hydrochloride (HCl.Pro$^P$(OPh-4-Cl)$_2$, 3). A mixture of 1-pyrroline trimer and di(4-chlorophenyl) phosphite was reacted using the procedure described for compound 1. Hydrochloride 3 was obtained by dissolving the crude phosphonate in ether saturated with gaseous HCl (white solid in 30% yield): mp. 160°–165° C. (dec.); $^1$H-NMR (D$_2$O) δ (ppm) 1.8–2.5 (m, 4H), 3.4 (m, 2H), 4.30 (m, 1H), 7.0 (m, 4H), 7.2 (m, 4H);

MS (FAB) m/e 372 (M– Cl)$^+$. Anal. ($C_{16}H_{17}NO_3PCl_3$):C, H, N.

EXAMPLE 23

Di(4-chlorophenyl) Piperidine-2-phosphonate Hydrochloride (HCl.Pip$^P$(OPh-4-Cl)$_2$, 4). The trimer of 2,3,4,5-tetrahydropyridine and di(4-chlorophenyl) phosphite were reacted using the procedure described for compound 2. The phosphonate hydrochloride 4 was obtained by reaction with HCl as described above in 55% yield: mp.>140° C. (dec); $^1$H-NMR (D$_2$O) δ (ppm) 1.3–2.1 (m, 6H), 3.2–3.5 (m, 2H), 4.0 (m, 1H), 6.86 (m, 4H), 7.1 (m, 4H); MS (FAB) m/e 386 (M–Cl)$^+$. Anal. (exact mass, HRMS) calcd. for $C_{17}H_{19}N_1O_3P_1Cl_2$ m/e 386.0479, found 386.0468.

EXAMPLE 24

Di(4-fluorophenyl) Piperidine-2-phosphonate Hydrochloride (HCl.Pip$^P$(OPh-4-F)$_2$, 5). A mixture of piperidine trimer (4.5 g, 54 mmole) and di(4-fluorophenyl)phosphite (14.8 g, 55 mmole) was heated at 90°–100° C. for 3 h under nitrogen. The resulted oil was cooled and dissolved in a mixture of 50 mL CH$_2$Cl$_2$ and 50 mL ether. The solution was saturated with dry HCl, the oil was separated and solidified after several hours. The solid was filtered, washed with ether and dried. The hygroscopic material was stirred in 200 mL dry ether for several hours and the yellowish solid was filtered and dried. The product was obtained in 54% yield (11.6 g) and used for subsequent reaction: mp. 155°–165° C. (dec); $^1$H NMR (D$_2$O) δ7.2-6.8 (m, 8H), 3.6-2.9 (m, 3H), 2.2-1.4 (m, 6H); MS (FAB) m/e 354 (M–Cl)$^+$. Anal. (exact mass, HRMS) calcd. for $C_{17}H_{19}N_1O_3P_1Cl_2$ m/e 354.1070, found 354.1098.

EXAMPLE 25

Dipeptide Synthesis: General Procedure. The hydrochloride of the phosphonates (1, 2, 3, 4 or 5) (5 retool) and triethyl amine (5 mmol) were dissolved in 25 mL CH$_2$Cl$_2$ and cooled to –10° C. A Cbz-blocked amino acid (5 mmol) was added and the mixture was stirred at –10° C. for 15 min. The coupling reagent DCC (6 mmol) in 25 mL CH$_2$Cl$_2$ was added and the mixture was stirred at –10° C. for 2 h and 20 h at r.t. The DCU precipitate was removed by filtration and the filtrate was evaporated. The residue was dissolved in 100 mL ethyl acetate and filtered. The organic layer was washed subsequently with 50 mL 1M HCl, water, 6% NaHCO$_3$, and water, and dried over MgSO$_4$. The filtrate was evaporated to give the crude dipeptide. Traces of DCU was removed by filtration of the crude dipeptide dissolved in 25 mL ether. The dipeptide was dried in vacuo and recrystallized from hexane-ether.

The Cbz group of the dipeptides were removed by hydrogenolysis or treatment with 30% HBr in acetic acid. The Cbz-blocked dipeptide (1–2 mmol) was dissolved in 100 mL methanol, one equivalent of conc. hydrochloric acid (1–2 mmol) and 5% Pd on carbon (0.5–1.0 g) were added, and the mixture was hydrogenated at r.t. for 2–3 h. After hydrogenation, the catalyst was removed and the filtrate was evaporated to give the deblocked dipeptide hydrochloride, which was recrystallized from methanol-ether, or ether. The Cbz-blocked dipeptide (1 mmol) can also be treated with 1 mL 30% HBr/AcOH and stirred at r.t. for 1 h. The mixture was protected against moisture during stirring. The solution was diluted with 50 mL dry ether and kept at 0° C. for 1–2 h. The hydrobromide of dipeptide precipitated, was filtered, washed with dry ether, and dried as a yellow-brown solid.

Diphenyl Alanylpyrrolidine-2-phosphonate Hydrochloride (HCl.Ala-Pro$^P$(OPh)$_2$, 6). Cbz-Ala-Pro$^P$(OPh)$_2$ was obtained as a thick oil in 90% yield: $^1$H-NMR (CDCl$_3$) δ (ppm) 1.3 (dd, 3H), 1.5–2.5 (m, 5H), 3.3–3.8 (m, 2H), 4.1 (m, 1H), 4.5 (m, 1H), 5.10 (m, 2H), 5.7 (dd, 1H), 7.0–7.4 (m, 15H). Hydrogenolysis of Cbz-Ala-Pro$^P$(OPh)$_2$ gave the product 6 as a hygroscopic solid in 65% yield: top. 80°–85° C.; $^1$H-NMR (D$_2$O) δ (ppm) 1.3–1.6 (dd, 3H), 1.5–2.4 (m, 5H), 3.3–3.7 (m, 2H), 4.25 (m, 1H), 4.35 (m, 1H), 6.9–7.4 (m, 10H); MS (FAB) m/e 375 (M–Cl)$^+$. Anal. (exact mass, HRMS) calcd. for $C_{19}H_{24}N_2O_4P_1$ m/e 375.1474, found 375.1549.

EXAMPLE 26

Diphenyl Alanylpiperidine-2-phosphonate Acetate (CH$_3$COOH.Ala-Pip$^P$(OPh)$_2$, 7). Cbz-Ala-Pip$^P$(OPh)$_2$ was obtained as a thick oil in 76% yield: $^1$H-NMR (CDCl$_3$) δ (ppm) 1.2–1.3 (dd, 3H), 1.5–2.4 (m, 6H), 3.6–3.8 (m, 2H), 4.5 (g, 1H), 5.10 (s, 2H), 5.6 (m, 1H), 5.8 (dd, 1H), 7.0–7.4 (m, 15H). Hydrogenolysis of Cbz-Ala-Pip$^P$(OPh)$_2$ using one equiv. of acetic acid gave the product 7 as a glass-like solid in 82% yield: mp. 60°–70° C.; $^1$H-NMR (CDCl$_3$) δ (ppm) 1.2–1.3 (dd, 3H), 1.5–2.4 (m, 6H), 2.0 (s, 3H), 3.5–4.0 (m, 2H), 4.2 (m, 1H), 5.6 (m, 1H), 7.0–7.4 (m, 10H), 7.2 (m, 3H); MS (FAB) m/e 389 (M–CH$_3$COO)$^+$. Anal. (exact mass, HRMS) calcd. for $C_{20}H_{26}N_2O_4P_1$ m/e 389.1630, found 389.1639.

EXAMPLE 27

Monophenyl Alanylpiperidine-2-phosphonate Acetate (CH$_3$COOH.Ala-Pip$^P$(OH)(OPh), 8). A small amount of the monophenyl ester 8 was isolated in 10% yield during the work-up of product 7 as a white solid: mp. 175°–180 ° C. (dec); $^1$H-NMR (D$_2$O) δ (ppm) 1.3 (m, 3H), 1.5–2.1 (m, 6H), 2.1 (s, 3H), 3.5 (m, 2H), 4.2 (m, 1H), 4.4 (m, 1H), 4.8 (dd, 1H), 7.0–7.4 (m, 5H). MS (FAB) m/e 313 (M –CH$_3$COO)$^+$. Anal. (exact mass, HRMS) calcd. for $C_{14}H_{22}N_2O_4P_1$ m/e 313.1317, found 313.1518.

EXAMPLE 28

Diphenyl Phenylalanylpyrrolidine-2-phosphonate Hydrobromide (HBr.Phe-Pro$^P$(OPh)$_2$, 9). Cbz-Phe-Pro$^P$(OPh)$_2$ was obtained as a thick oil which partially solidified in 61% yield: $^1$H-NMR (CDCl$_3$) δ (ppm) 1.0–2.0 (m, 4H), 3.25 (d, 2H), 3.0–3.5 (m, 3H), 4.7 (m, 1H), 5.05 (m, 1H), 5.15 (s, 2H), 5.35 (m, 1H), 7.0–7.4 (m, 20H). Deblocking of Cbz-Phe-Pro$^P$(OPh)$_2$ with 30% HBr/AcOH gave the product 9 as a yellow-brown hygroscopic solid in 33% yield: mp.>140° C. (dec.); $^1$H-NMR (D$_2$O) δ 1.0–2.0 (m, 4H), 3.0–3.4 (m, 3H), 3.3 (d, 2H), 4.3 (m, 1H), 4.7 (m, 1H), 7.0–7.4 (m, 15H); MS (FAB) m/e 451 (M–Br)$^+$. Anal. (exact mass, HRMS) calcd. for $C_{25}H_{28}N_2O_4P_1$ m/e 451.1786, found 451.1769.

EXAMPLE 29

Diphenyl Lysylpyrrolidine-2-phosphonate Dihydrobromide (2HBr.Lys-Pro$^P$(OPh)$_2$, 10). The lysine derivative Cbz-Lys(Cbz)-OH was reacted with phosphonate 1 to give Cbz-Lys(Cbz)-Pro$^P$(OPh)$_2$ as a thick oil in 86% yield: $^1$H-NMR (CDC$_3$) δ (ppm) 1.0–2.5 (m, 8H), 3.0–4.0 (m, 4H), 4.5 (m, 1H), 4.9 (m, 1H), 5.1 (2s, 4H), 5.5–5.8 (dd, 2H), 7.0–7.4 (m, 20H). Treatment of Cbz-Lys(Cbz)-Pro$^P$(OPh)$_s$ with 30% HBr/AcOH gave the product 10 as a yellow brown hygroscopic solid in 64% yield: mp. >85° C. (dec.); $^1$H-NMR (D$_2$O) δ (ppm) 1.2–2.5 (m, 8H), 2.8–3.0 (m, 4H), 3.55 (t, 1H), 4.1–4.5 (m, 2H), 7.0–7.5 (m, 10H); MS (FAB)

m/e 432 (M −H −2Br)⁺. Anal. (exact mass, HRMS) calcd. for $C_{22}H_{31}N_3O_4P_1$ m/e 432.2052, found 432.2059.

EXAMPLE 30

Diphenyl Lysylpiperidine-2-phosphonate Dihydrochloride (2HCl.Lys-Pip$^P$(OPh)$_2$, 11). The lysine derivative Cbz-Lys(Cbz)-OH was reacted with phosphonate 2 to give diphenyl Cbz-Lys(Cbz)-Pip$^P$(OPh)$_2$ as a thick oil in 65% yield: $^1$H-NMR (CDCl$_3$) δ (ppm) 1.0–2.0 (m, 12H), 3.0–3.2 (m, 2H), 3.4–3.8 (m, 2H), 4.4–4.8 (m, 1H), 5.1 (2s, 4H), 5.5–5.9 (m, 2H), 7.0–7.5 (m, 20H). Hydrogenolysis of Cbz-Lys(Cbz)-Pip$^P$(OPh)$_2$ gave the product 11 as a white solid in 54% yield: mp. 110°–115° C. (dec.); $^1$H-NMR (D$_2$O) δ (ppm) 1.3–2.1 (m, 12H), 2.8–3.0 (m, 2H), 3.3–3.7 (m, 2H), 4.3–4.5 (m, 1H), 7.0–7.4 (m, 10H); MS (FAB) m/e 446 (M−H−2Cl)⁺. Anal. (exact mass, HRMS) calcd. for $C_{23}H_{33}N_3O_4P_1$ m/e 446.2208, found 446.2213.

EXAMPLE 31

Di(4-chlorophenyl) Alanylpyrrolidine-2-phosphonate Hydrochloride (HCl-Ala-Pro$^P$(OPh-4-Cl)$_2$, 12). Benzyloxycarbonylalanine (Cbz-Ala) was reacted with phosphonate 3 to give Cbz-Ala-Pro$^P$(OPh-4-Cl)$_2$ (12a) as a semi-solid in 41% yield: $^1$H-NMR (CDCl$_3$) δ (ppm) 1.25–1.35 (dd, 3H), 1.8–2.5 (m, 4H), 3.3–3.9 (m, 2H), 4.55 (m, 1H), 5.0 (m, 1H), 5.1 (s, 2H), 5.5–5.7 (dd, 1H), 7.0–7.4 (m, 13H); MS 12 as a hygroscopic white solid in 53% yield: mp. 88°–91° C.; $^1$H-NMR (D$_2$O) δ (ppm) 1.25–1.35 (dd, 3H), 1.7–2.2 (m, 4H), 3.2–3.6 (m, 2H), 4.25 (q, 1H), 4.6–4.8 (m, 1H), 6.7–7.0 (m, 8H), MS (FAB) m/e 443 (M−Cl)⁺. Anal. (Exact mass, HRMS) calcd. for $C_{19}H_{22}N_2O_4Cl_2P_1$ m/e 443.0694, found 443.0649.

EXAMPLE 32

Di(4-chlorophenyl) Alanylpiperidine-2-phosphonate Hydrochloride (HCl.Ala-Pip$^P$(OPh-4-Cl)$_2$, 13). Benzyloxycarbonylalanine (Cbz-Ala) was reacted with phosphonate 4 to give Cbz-Ala-Pip$^P$(OPh-4-Cl)$_2$ (13a) as a thick oil in 38% yield: $^1$H-NMR (CDCl$_3$) δ (ppm) 1.25–1.35 (2d, 3H), 1.4–2.3 (m, 6H), 3.3–3.9 (m, 2H), 4.5–4.8 (m, 1H), 5.1 (s, 2H), 5.4 (m, 1H), 5.8 (dd, 1H), 7.0–7.4 (m, 8H), 7.35 (s, 5H); MS (FAB) m/e 591 (M+1)⁺. Hydrogenolysis of Cbz-Ala-Pip$^P$(OPh-4-Cl)$_2$ gave 13 as a hygroscopic solid in 49% yield: top. 110°–115° C. (dec.); $^1$H-NMR (D$_2$O) δ (ppm) 1.35 (d, 3H), 1.1–2.0 (m, 6H), 3.35 (m, 2H), 3.70 (m, 1H), 4.40 (m, 1H), 6.8–7.4 (m, 8H); MS (FAB) m/e 457 (M−Cl)⁺. Anal. (exact mass, HRMS) calcd. for $C_{20}H_{24}N_2O_4Cl_2P_1$ m/e 457.0851, found 457.0834.

EXAMPLE 33

Di(4-fluorophenyl) Alanyl-piperidine-2-phosphonate Hydrochloride (HCl.Ala-Pip$^P$(OPh-4-F)$_2$, 14). Benzyloxycarbonylalanine (Cbz-Ala) was reacted with phosphonate 5 to give Cbz-Ala-Pip$^P$(OPh-4-F)$_2$ (14a) as a thick oil in 25% yield: TLC (CHCl$_3$:Acetone=9:1) R$_f$=0.45; $^1$H NMR (DMSO) δ 7.35(s, 5H), 7.4–6.9 (m, 8H), 5.4–5.1 (m, 1H), 5.0 (s, 2H), 4.7–4.3 (m, 1H), 3.9 (m, 1H), 3.5–3.1 (m,2H), 2.0-1.1 (m, 6H), 1.25 (rid, 3H); MS (FAB) m/e 559 (M+H)⁺. The hydrogenolysis of 14a (1.3 g, 2.3 mmole) in methanol in the presence of 1 equivalent of HCl and 5% Pd/C gave a hygroscopic solid which was recrystallized from methanol and ether in 57% yield (0.6 g): mp. 105°–115° C. (dec) $^1$H NMR (D$_2$O) δ 6.85-6.55 (m, 8H), 4.5–4.25 (m, 2H), 3.7–3.2 (m, 2H), 2.0–1.1 (m, 6H), 1.46–1.32 (d, 3H); MS (FAB) m/e 425 (M−Cl)⁺. Anal. (exact mass, HRMS) calcd. for $C_{20}H_{24}N_2O_4PF_2$ m/e 425.1442, found. 425.1290.

It is obvious that those skilled in the art may make modifications to the invention without departing from the spirit of the invention or the scope of the subjoined claims and their equivalents.

What is claimed is:

1. A compound having the following structures:

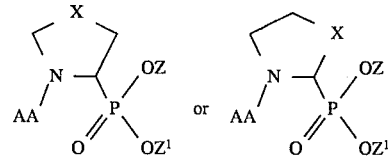

or a pharmaceutically acceptable salt thereof, wherein

Z and $Z^1$ are the same or different and are selected from the group consisting of $C_{1-6}$ perfluoralkyl, phenyl, phenyl substituted with J, phenyl disubstituted with J, phenyl trisubstituted with J, and pentafluorophenyl;

J is selected from the group consisting of halogen $C_{1-6}$ alkyl, $C_{1-6}$ perfluoroalkyl, $C_{1-6}$ alkoxy, NO$_2$, CN, OH, CO$_2$H, amino $C_{1-6}$ alkylamino, $C_{2-12}$ dialkylamino, $C_{1-6}$ acyl, and $C_{1-6}$ alkoxy—CO—, and $C_{1-6}$ alkyl—S—;

X is selected from the group consisting of
(a) a single bond,
(b) —CH$_2$—,
(c) —CH$_2$CH$_2$—,
(d) —CH$_2$CH$_2$CH$_2$—,
(e) —CH$_2$CH$_2$CH$_2$CH$_2$—,
(f) —Y—
(g) —CH$_2$—Y—,
(h) —Y—CH$_2$—, and
(i) —H, H—;

wherein Y is O or S; and

AA is attached through the carboxylic end and is selected from the group consisting of
(a) the structure NH$_2$—CHR—CO—
where R is selected from the group consisting of $C_{1-6}$ alkyl and $C_{1-6}$ fluorinated alkyl,
(b) a side chain blocked or unblocked alpha amino acid residue with the L, D or DL configuration at the α-carbon atom selected from the group consisting of alanine, valine, leucine, isoleucine, proline, methionine, methionine sulfoxide, phenylalanine, tryptophan, serine, threonine, cysteine, asparagine, glutamine, aspartic acid, glutamic acid, lysine, arginine, histidine, phenylglycine, norleucine, norvaline, alpha-aminobutyric acid, citrulline, hydroxyproline, ornithine, homoarginine, O-methylserine, O-ethylserine, S-methylcysteine, S-ethylcysteine, S-benzylcysteine, [NH$_2$—CH(CH$_2$CHEt$_2$)—COOH] NH$_2$—CH(CH$_2$CHEt$_2$)—CO—, alpha-aminoheptanoic acid, [NH$_2$—CH(CH$_2$-1-napthyl)—COOH, NH$_2$—CH(CH$_2$-2-napthyl)—COOH, NH$_2$—CH(CH$_2$-cyclohexyl)—COOH, NH$_2$—CH(CH$_2$-cyclopentyl)—COOH, NH$_2$—CH(CH$_2$-cyclobutyl) —COOH, NH$_2$—CH(CH$_2$-cyclopropyl)—COOH,]NH$_2$—CH(CH$_2$-1-napthyl)—CO—, NH$_2$—CH (CH$_2$-2-napthyl)—CO—, NH$_2$—CH(CH$_2$-cyclohexyl)—CO—, NH$_2$—CH(CH$_2$-cyclopentyl)—CO—, NH$_2$—CH(CH$_2$-cyclobutyl)—CO—, NH$_2$—CH(CH$_2$-cyclopropyl)—CO—5,5,5-trifluoroleucine, and hexafluoroleucine,
(c) an amino acid residue selected from the group consisting of beta-alanine, glycine, epsilon-aminocaproic acid, and sarcosine, and (d) C$_6$H$_5$CH$_2$OCO—.

2. A compound having the following structures:

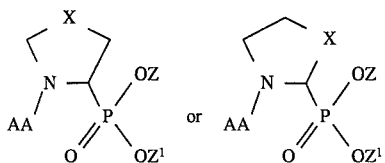

or a pharmaceutically acceptable salt thereof, wherein

Z and Z$^1$ are the same or different and are selected from the group consisting of C$_{1-6}$ perfluoralkyl, phenyl, phenyl substituted with J, phenyl disubstituted with J, phenyl trisubstituted with J, and pentafluorophenyl;

J is selected from the group consisting of halogen C$_{1-6}$ alkyl, C$_{1-6}$perfluoroalkyl, C$_{1-6}$ alkoxy, NO$_2$, CN, OH, CO$_2$H, amino, C$_{1-6}$alkylamino, C$_{2-12}$ dialkylamino, C$_{1-6}$ acyl, and C$_{1-6}$ alkoxy—CO—, and C$_{1-6}$alkyl—S—;

X is selected from the group consisting of —CH$_2$— and —CH2CH$_2$— and,

AA is attached through the carboxylic end and is selected from the group consisting of
(a) the structure NH$_2$—CHR—CO—
where R is selected from the group consisting of C$_{1-6}$ alkyl and C$_{1-6}$ fluorinated alkyl,
(b) a side chain blocked or unblocked alpha amino acid residue with the L, D or DL configuration at the α-carbon atom selected from the group consisting of alanine, valine, leucine, isoleucine, proline, methionine, methionine sulfoxide, phenylalanine, tryptophan, serine, threonine, cysteine, asparagine, glutamine, aspartic acid, glutamic acid, lysine, arginine, histidine, phenylglycine, norleucine, norvaline, alpha-aminobutyric acid, citrulline, hydroxyproline, ornithine, homoarginine, O-methylserine, O-ethylserine, S-methylcysteine, S-ethylcysteine, S-benzylcysteine, [NH$_2$—CH(CH$_2$CHEt$_2$)—COOH] NH$_2$—CH(CH$_2$CHEt$_2$)—CO—, alpha-aminoheptanoic acid, [NH$_2$—CH(CH$_2$-1-napthyl)—COOH, NH$_2$—CH(CH$_2$-2-napthyl)—COOH, NH$_2$—CH(CH$_2$-cyclohexyl)—COOH, NH$_2$—CH(CH$_2$-cyclopentyl)—COOH, NH$_2$—CH(CH$_2$-cyclobutyl)—COOH, NH$_2$—CH(CH$_2$-cyclopropyl)—COOH,]NH$_2$—CH(CH$_2$-1-napthyl)—CO—, NH$_2$—CH (CH$_2$-2-napthyl)—CO—, NH$_2$—CH(CH$_2$-cyclohexyl)—CO—, NH$_2$—CH(CH$_2$-cyclopentyl)—CO—, NH$_2$—CH(CH$_2$-cyclobutyl)—CO—, NH$_2$—CH(CH$_2$-cyclopropyl)—CO—5,5,5-trifluoroleucine, and hexafluoroleucine,
(c) an amino acid residue selected from the group consisting of beta-alanine, glycine, epsilon-aminocaproic acid, and sarcosine,
(d) H, and
(e) C$_6$H$_5$CH$_2$OCO—.

3. A compound according to claim 2 wherein

Z and Z$^1$ are selected from the group consisting of phenyl, phenyl substituted with J, and phenyl disubstituted with J.

4. A compound according to claim 3 wherein

AA is attached through the carboxylic end and is selected from the group consisting of
(a) the structure NH$_2$—CHR—CO—
where R is selected from the group consisting of C$_{1-6}$ alkyl and C$_{1-6}$ fluorinated alkyl,
(b) a side chain blocked or unblocked alpha amino acid residue with the I, D or DL configuration at the α-carbon atom selected from the group consisting of alanine, voline, ieucine, isoleucine, proline, methionine, methionine sulfoxide, phenylalanine, tryptophan, serine, threonine, cysteine, asparagine, glutamine, aspartic acid, glutamic acid, lysine, arginine, histidine, phenylglycine, norleucine, norvaline, alpha-aminobutyric acid, citrulline, hydroxyproline, ornithine, homoarginine, O-methylserine, O-ethylserine, S-methylcysteine, S-ethylcysteine, S-benzylcysteine, [NH$_2$—CH(CH$_2$CHEt$_2$)—COOH]NH$_2$—CH(CH$_2$CHEt$_2$)—CO—, alpha-aminoheptanoic acid, [NI]$_2$—CH(CH$_2$-1-napthyl)—COOH, NH$_2$—CH(CH$_2$-2-napthyl)—COOH, NH$_2$—CH(CH$_2$-cyclohexyl)—COOH, NH$_2$—CH(CH$_2$-cyclopentyl)—COOH, NH$_2$—CH(CH$_2$-cyclobutyl)—COOH, NH$_2$—CH(CH$_2$-cyclopropyl)—COOH,] NH$_2$—CH(CH$_2$-1-naphyl)—CO—, NH$_2$—CH(CH$_2$-2-napthyl)—CO—, NH$_2$—CH(CH$_2$—cyclohexyl)—CO—, NH$_2$—CH(CH$_2$-cyclopentyl)—CO—, NH$_2$—CH(CH$_2$-cyclobutyl)—CO—, NH$_2$—CH(CH$_2$-cyclopropyl)—CO—, 5,5,5-trifluoroleucine, and hexafluoroleucine, and
(c) an amino acid residue selected from the group consisting of beta-alanine, glycine, epsilon-aminocaproic acid, and sarcosine.

5. A compound or pharmaceutically acceptable salt of the compound selected from the group consisting of:
(a) diphenyl pyrrolidine-2-phosphonate hydrochloride (HCl.Pro$^P$(OPh)$_2$),
(b) diphenyl piperidine-2-phosphonate hydrochloride (HCl.Pip$^P$(OPh)$_2$),
(c) di(4-chlorophenyl) pyrrolidine-2-phosphonate hydrochloride (HCl.Pro$^P$(OPh-4-Cl)$_2$),
(d) di(4-chlorophenyl) piperidine-2-phosphonate hydrochloride (HCl.Pip$^P$(OPh-4-Cl)$_2$),
(e) di(4-fluorophenyl) piperidine-2-phosphonate hydrochloride (HCl.Pip$^P$(OPh-4-F)$_2$),
(f) diphenyl alanylpyrrolidine-2-phosphonate hydrochloride (HCl.Ala-Pro$^P$ (OPh)$_2$),
(g) Cbz-Ala-Pro$^P$(OPh)$_2$,
(h) Ala-Pip$^P$(OPh)$_2$,
(i) Cbz-Ala-Pip$^P$(OPh)$_2$,
(j) Phe-Pro$^P$(OPh)$_2$,
(k) Cbz-Phe-Pro$^P$(OPh)$_2$,
(l) Lys-Pro$^P$(OPh)$_2$,
(m) Cbz-Lys(Cbz)-Pro$^P$(OPh)$_2$,
(n) Lys-Pip$^P$(OPh)$_2$,
(o) Cbz-Lys(Cbz)-Pip$^P$(OPh)$_2$,
(p) Ala-Pro$^P$(OPh-4-Cl)$_2$,
(q) Cbz-Ala-Pro$^P$(OPh-4-Cl)$_2$,
(r) Ala-Pip$^P$(OPh-4-Cl)$_2$,
(s) Cbz-Ala-Pip$^P$(OPh-4-Cl)$_2$,
(t) Ala-Pip$^P$(OPh-4-F)$_2$, and
(u) Cbz-Ala-Pip$^P$(OPh-4-F)$_2$.

6. A method of inhibiting dipeptidyl peptidase IV in mammals consisting of treating a mammal with a therapeutically effective amount of the compound in claim 1.

7. A method of preventing tissue transplant rejection in mammals consisting of treating a mammal with a therapeutically effective amount of the compound in claim 1.

8. A compound according to claim 1 wherein AA is a side chain blocked or unblocked alpha amino acid residue with the L configuration at the α-carbon.

9. A compound according to claim 1 wherein AA is a side chain blocked or unblocked alpha amino acid residue with the D configuration at the α-carbon.

10. A compound according to claim 1 wherein AA is a side chain blocked or unblocked alpha amino acid residue with the DL configuration at the α-carbon.

11. A compound according to claim 4 wherein AA is a side chain blocked or unblocked alpha amino acid residue with the L configuration at the α-carbon.

12. A compound according to claim 4 wherein AA is a side chain blocked or unblocked alpha amino acid residue with the D configuration at the α-carbon.

13. A compound according to claim 4 wherein AA is a side chain blocked or unblocked alpha amino acid residue with the DL configuration at the α-carbon.

* * * * *